United States Patent [19]
Nishimoto et al.

[11] Patent Number: 6,140,487
[45] Date of Patent: Oct. 31, 2000

[54] DNA ENCODING KOJIBIOSE PHOSPHORYLASE OBTAINABLE FROM THERMOANAEROBIUM, IT'S PREPARATION AND USES

[75] Inventors: Tomoyuki Nishimoto; Michio Kubota; Hiroto Chaen; Toshio Miyake, all of Okayama, Japan

[73] Assignee: Kabushiki Kaisha Hayashibara Seibutsu Kagaku Kenkyujo, Okayama, Japan

[21] Appl. No.: 09/188,404

[22] Filed: Nov. 10, 1998

Related U.S. Application Data

[62] Division of application No. 08/966,388, Nov. 7, 1997, Pat. No. 5,965,412.

[30] Foreign Application Priority Data

Nov. 8, 1996 [JP] Japan ..................................... 8-311235
Mar. 3, 1997 [JP] Japan ..................................... 9-61710

[51] Int. Cl.$^7$ .............................. C07H 21/04; C12N 9/12
[52] U.S. Cl. ..................... 536/23.2; 435/194; 435/320.1; 435/252.3; 435/100
[58] Field of Search ........................... 536/23.2; 435/100, 435/252.3, 194, 320.1

[56] References Cited

U.S. PATENT DOCUMENTS

Re. 33,047 9/1989 Miyake et al. ......................... 127/46.3
4,521,252 6/1985 Miyake et al. ......................... 127/46.3

FOREIGN PATENT DOCUMENTS 58-23799 2/1983 Japan .
58-72598 4/1983 Japan .
1 390 065 4/1975 United Kingdom .

OTHER PUBLICATIONS

Hatt et al (eds.), *Catalogue of Bacteria and Phages*, 18th Ed., American Type Culture Collection, USA (1992).
Sambrook et al, *Molecular Cloning: A Laboratory Manual*, 2nd Ed., Cold Spring Harbor Laboratory Press (1989).
*Enzyme Handbook*, Asakura–Shoten Publisher, Tokyo, Japan (1982).
Database WPI; Derwent Publications Ltd., London, GB; AN 91–076855; XP002110119 & JP 03 02257 A (Showa Sangyo Co.), Jan. 31, 1991 *Abstract*.
Database WPI; Derwent Publications Ltd., London, GB; AN 95–125550; XP002110120 & 07 046991 A (Kikkoman Corp.), Feb. 21, 1995 *Abstract*.
Aisaka et al, "Purification and Characterization of Trehalose Phosphorylase from *Catellatospora ferruginea*", *Biosci. Biotech. Biochem.* 62(4):782–787 (1998).
Fujii et al, "Oligosaccharides produced by the transglucosidation action of Protaminobacter rubrum α–glucosidase"; Chemical Abstracts; Database Accession No. 105:222353, 1985.
Kitao et al, "Formation of Kojiboise and Nigerose by Sucrose Phosphorylase", *Biosci. Biotech. Biochem.* 58(4):790–791 (1994).
Takewaki et al, "Substrate Specificity and Subsite Affinities of Honeybee α–Glucosidase II", *Biosci. Biotech, Biochem.* 57(9):1508–1513 (1993).

*Primary Examiner*—Ponnathapu Achutamurthy
*Assistant Examiner*—Bradley S. Mayhew
*Attorney, Agent, or Firm*—Browdy and Neimark

[57] ABSTRACT

A kojibiose phosphorylase which hydrolyzes kojibiose in the presence of an inorganic phosphoric acid to form D-glucose and β-D-glucose-1-phosphoric acid, forms kojibiose and an inorganic phosphoric acid from β-D-glucose-1-phosphoric acid, and catalyzes the transfer reaction of glucosyl group to other saccharides using β-D-glucose-1-phosphoric acid as a saccharide donor. The enzyme is obtainable from natural sources such as microorganisms of the genus Thermoanaerobium, and obtainable by recombinant technology.

16 Claims, 5 Drawing Sheets

DNA ENCODING KOJIBIOSE PHOSPHORYLASE OBTAINABLE FROM THERMOANAEROBIUM, IT'S PREPARATION AND USES

This is a division of parent application Ser. No. 08/966,388, filed Nov. 7, 1997, now U.S. Pat. No. 5,965,412.

BACKGROUND OF THE INVENTION

1. Field of the Invention

The present invention relates to a novel kojibiose phosphorylase, its preparation and uses, more particularly, to a novel kojibiose phosphorylase which hydrolyzes kojibiose in the presence of an inorganic phosphoric acid and/or its salt (hereinafter abbreviated as "inorganic phosphoric acid" throughout the present specification, if not any inconvenience will arise) to form D-glucose and β-D-glucose-1-phosphoric acid and/or its salt (hereinafter abbreviated as "β-D-glucose-1-phosphoric acid" throughout the present specification, if not any inconvenience will arise), and which, in reverse, forms kojibiose and inorganic phosphoric acid from β-D-glucose-1-phosphoric acid and D-glucose, and to the processes of the kojibiose phosphorylase, saccharide compositions containing glucosyl-transferred saccharides produced by using the kojibiose phosphorylase, and compositions containing the saccharide compositions.

2. Description of the Prior Art

Recently, oligosaccharides such as maltose and trehalose and functions thereof have become to be highlighted, and have been studied on their unique and different processes in view of various aspects. There has been known that phosphorylases such as maltose, trehalose, sucrose, cellobiose, and laminaribiose phosphorylases can be used as methods for producing the above oligosaccharides. Various microorganisms are known as sources of these phosphorylases.

The activities and resources of these phosphorylases are summarized in "Enzyme Handbook", published by Asakura-Shoten Publisher, Tokyo, Japan (1982). However, no phosphorylase capable of forming kojibiose has been known, and the actual supply has been desired.

SUMMARY OF THE INVENTION

The present invention provides a novel enzyme, kojibiose phosphorylase, process thereof, saccharide compositions containing the glucosyl-transferred saccharides prepared by using the enzyme, and uses thereof.

To solve the above object and to obtain an unknown kojibiose phosphorylase, the present inventors widely screened microorganisms which produce such an enzyme. As a result, they found that *Thermoanaerobium brockii*, ATCC 35047, belonging to the genus Thermoanaerobium, produces a novel kojibiose phosphorylase and established the preparation. They also obtained a novel and/or conventionally known glucosyl-transferred saccharides, which can be produced by contacting the enzyme with β-D-glucose-1-phosphoric acid as a saccharide donor in the presence of saccharides, and a process for compositions containing the above novel and/or conventionally known saccharides. Thus, they accomplished this invention.

BRIEF DESCRIPTION OF THE ACCOMPANYING DRAWINGS

DETAILED DESCRIPTION OF THE INVENTION

Figure 1:
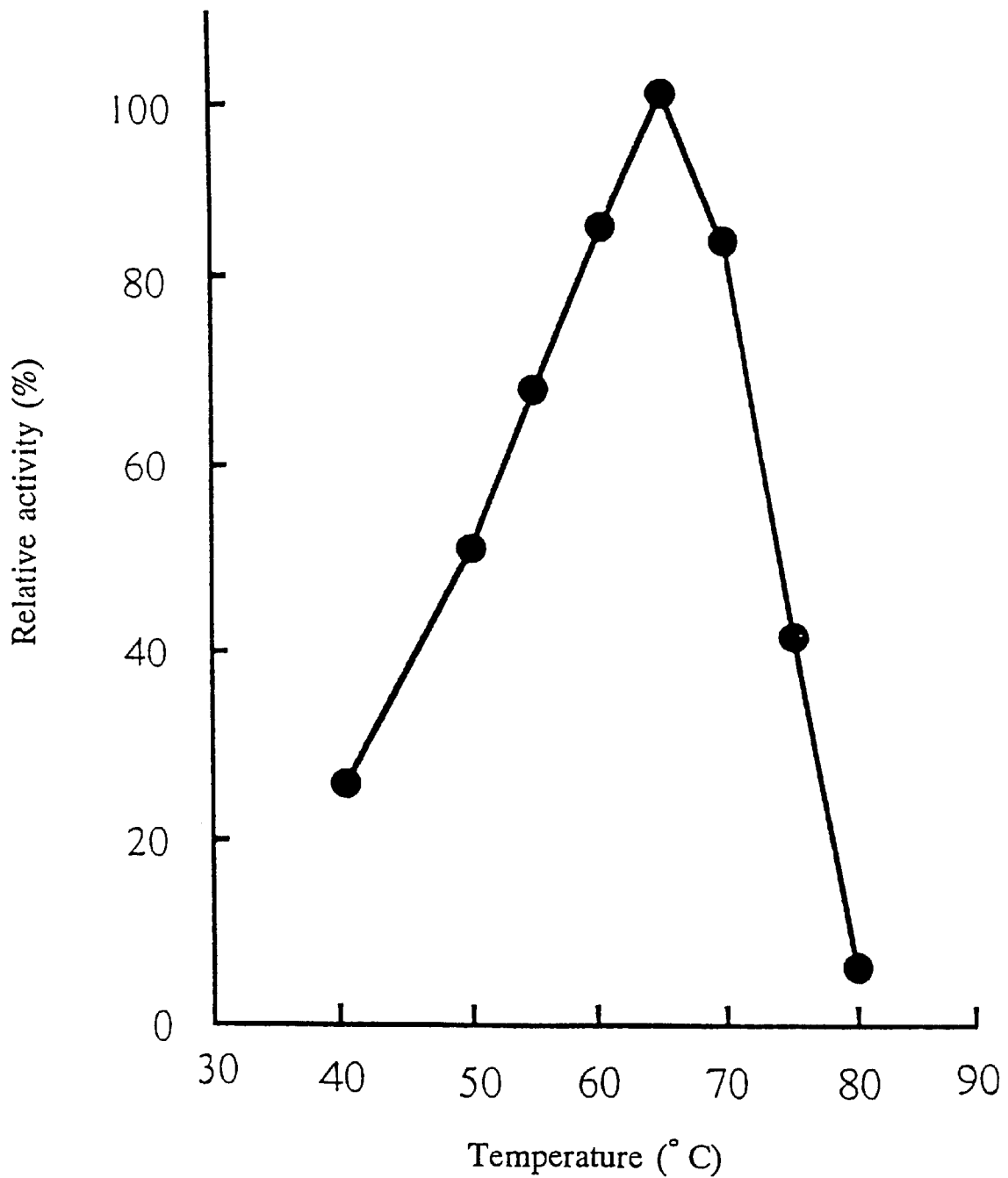
FIG. 1 shows the influence of temperatures on the activity of kojibiose phosphorylase according to the present invention.

The kojibiose phosphorylase according to the present invention includes all enzymes which hydrolyze kojibiose in the presence of inorganic phosphoric acid to form D-glucose and β-D-glucose-1-phosphoric acid, and the origin of such enzymes are not restricted. The present kojibiose phosphorylase has the following action and physicochemical properties:

(1) Action
  (a) Hydrolyzing kojibiose in the presence of an inorganic phosphoric acid to form D-glucose and β-D-glucose-1-phosphoric acid;
  (b) Forming kojibiose and an inorganic phosphoric acid from D-glucose and β-D-glucose-1-phosphoric acid, and catalyzing the transfer reaction of glucosyl group to other saccharides using β-D-glucose-1-phosphoric acid as a saccharide donor;
(2) Molecular weight 83,000±5,000 daltons on SDS-PAGE;
(3) Isoelectric point pI 4.4±0.5 on electrophoresis using ampholyte,
(4) Optimum temperature About 65° C. when incubated at pH 5.5 for 30 min;
(5) Optimum pH About 5.5 when incubated at 60° C. for 30 min;
(6) Thermal stability Stable up to a temperature of about 65° C. when incubated at pH 5.5 for one hour;
(7) pH Stability Stable at pHs of about 5.5–10.0 when incubated at 4° C. for 24 hours; and
(8) Activity inhibition Inhibited by one mM $Hg^{++}$.

More concretely, the kojibiose phosphorylase includes proteins which have the amino acid sequence of SEQ ID NO:1, SEQ ID NO:2, or SEQ ID NO:3 as a partial amino acid sequence, and as a whole, have the amino acid sequence of SEQ ID NO:4 and functional equivalents thereof. The working "functional equivalents thereof" means proteins which still hold substantially the same activity of the kojibiose phosphorylase, and have the amino acid sequence of the enzyme where one or more amino acids are replaced with different ones, one or more amino acids are added to the N- and/or C-termini or inserted into the internal amino acid sequence, one or more amino acids in the N- and/or C-terminal regions are deleted, and one or more amino acids in the internal amino acid sequence are deleted. The kojibiose phosphorylase as mentioned above includes any one of those separated from natural resources such as cultures of microorganisms which produce the enzyme, mutants thereof obtained by treating with mutagens, and those which are artificially synthesized by applying recombinant DNA and peptide-synthesizing technologies. As mentioned below, according to the present invention, the desired enzyme is obtained both from the natural resources and by recombinant technology.

The DNA according to the present invention includes all the above DNAs which encode the present kojibiose phosphorylase. Examples of such DNAs are those which contain the nucleotide sequence of SEQ ID NO:5 and encode the amino acid sequence of SEQ ID NO:4, and functional equivalents thereof. The working "functional equivalents thereof" means DNAs which encode proteins with substantially retaining the same activity as the kojibiose phosphorylase, and have the nucleotide sequence of SEQ ID NO:5 where one or more bases are replaced with different ones, one or more bases are added to the 5'- and/or 3'-termini or inserted into the internal nucleotide sequence, one or more bases in the 5'- and/or 3'-terminal regions or in the internal nucleotide sequence are deleted, and complementary ones thereof. These functional equivalents include DNAs which are variants of SEQ ID NO:5 where one or more bases are replaced with different ones without altering the amino acid sequence encoded by SEQ ID NO:5. In addition to the above DNAs, the present DNA includes other DNAs where the 5'- and/or 3'-termini are linked to one or more DNAs, other than those encoding the kojibiose phosphorylases, such as start codon initiators, stop codons, Shine-Dalgarno sequence, nucleotide sequences encoding signal peptides, recognition sequences by appropriate restriction enzymes, promotors, enhancers, and terminators.

Resources and preparations of these DNAs are not specifically restricted in the present invention. For example, microorganisms of the genus Thermoanaerobium including *Thermoanaerobium brockii*, ATCC 35047, as natural resources of the DNAs, can be mentioned. The present DNA can be obtained by collecting DNA fractions from the cell debris of cultured microorganisms. The collected DNA per se can be used in the present invention, and it can be prepared into an extremely favorable recombinant DNA by introducing a fragment containing the DNA into a self-replicable vector; the recombinant DNA can be generally obtained by applying the recombinant DNA technology in general to the above DNA to obtain a gene library, and applying a selection method such as hydridization method for selecting the desired recombinant DNA from the gene library based on the nucleotide sequence, which encodes the present kojibiose phosphorylase, such as SEQ ID NO:5. The recombinant DNA thus obtained can be amplified when cultured transformants obtained by introducing into appropriate hosts such as microorganisms of the genus Escherichia, followed by applying the alkali-SDS method in general to the cultures to easily obtain a desired amount of the present DNA. The present DNA can be easily obtained by applying the PCR method in a conventional manner using as a template the disrupted cells of the above microorganisms or the DNA collected from the cells, and using as a primer a DNA chemically synthesized based on SEQ ID NO:5, or by chemically synthesizing a DNA containing SEQ ID NO:5. The above functional equivalents of the present DNA can be obtained, for example, by applying the site-directed mutagenesis to the above recombinant DNA, or applying the PCR method using both the recombinant DNA as a template and a chemically synthesized DNA containing a nucleotide sequence, which was converted into the desired nucleotide sequence, as a primer.

The present DNA includes those in the form of a recombinant DNA which is introduced into a self-replicable vector. As described above, these recombinant DNAs are extremely useful in preparing the present DNA, and are also useful in producing the present kojibiose phosphorylase. Once the desired DNA is obtained as described above, those recombinant DNAs can be relatively-easily obtained by applying the recombinant DNA technology in general to insert the DNA into an appropriate vector. Examples of such a vector are those which have a property of replicating in appropriate hosts plasmid. The following vectors can be arbitrarily used in the present invention; pUC18, Bluescrip-tII SK(+), pKK223-3, and λgt.λC which require microorganisms of the genus Escherichia as hosts; pUB110, pTZ4, pC194, ρ11, φ1, and φ105 which microorganisms of the genus Bacillus as hosts; and pHY300PLK, pHV14, TRp7, YEp7, and pBS7 which require at least two types of hosts. Referring to an example of method for inserting the present DNA into the vectors, an appropriate vector and either the present DNA thus obtained or a DNA containing the present DNA are cleaved with a restriction enzyme, and the formed DNA fragments and vector fragments are ligated. Examples of such a restriction enzyme suitably used are Acc I, Bam HI, Bgl II, Bst XI, Eco RI, Hind III, Not I, Pst I, Sac I, Sal I, Sma I, Spe I, Xba I, and Xho I. In the case of ligating the DNA and vector fragments, for example, chemically synthesized DNAs, having appropriate recognition sequences for the restriction enzymes, can be used. To ligate DNAs with others they are contacted with DNA ligases intra- and extra-cellularly after annealing.

The present DNA includes those in the form of a transformant into which the DNA is introduced. Such a transformant is extremely useful to obtain the present kojibiose phosphorylase and DNA. For example, microorganisms of the genera Escherichia and Bacillus, actinomyces, and yeasts can be arbitrarily used as host microorganisms for the transformant. The transformant can be usually obtained by introducing the aforesaid recombinant DNA into an appropriate host; when used a microorganism of the genus Escherichia, the microorganism and the recombinant DNA are cultured in the presence of calcium ion, while the competent cell and protoplast methods are applied when used a microorganism of the genus Bacillus. The aforesaid methods for preparing the present DNA are in themselves conventional ones used in the art as described, for example, by J. Sumbruck et al. in *"Molecular Cloning A Laboratory Manual"*, 2nd edition, published by Cold Spring Harbor Laboratory Press (1989).

The present process for producing kojibiose phosphorylase is characterized in that it comprises culturing a microorganism which produces the enzyme, and collecting the produced enzyme from the culture. The genus and species of such microorganisms and cultivation methods used in the present invention are not specifically restricted. Examples of such microorganisms include those which belong to the genus Thermoanaerobium, preferably, *Thermoanaerobium brockii*, ATCC 35047, and transformants obtained by introducing the present DNA into appropriate host microorganisms.

Any natural- and synthetic-nutrient culture media can be used for culturing the microorganisms used in the present process as long as the microorganisms can grow therein and produce the present enzyme. The carbon sources used in the present invention are those which can be utilized by the microorganisms; for example, saccharides such as maltose, trehalose, dextrins, and starches, and natural substances which contain saccharides such as molasses and yeast extracts can be used. The concentration of these carbon sources contained in the culture media is chosen depending on their types. For example, preferable saccharide concentrations are not higher than 20 w/v %, and not higher than 5 w/v % with respect to the microorganisms' growth and proliferation. The nitrogen sources used in the present invention are, for example, inorganic nitrogen-containing compounds such as ammonium salts and nitrates, and organic nitrogen-containing compounds such as urea, corn steep liquor, casein, peptone, yeast extract, and meet extract. If necessary, inorganic compounds, for example, salts of calcium, magnesium, potassium, sodium, phosphoric acid, manganese, zinc, iron, copper, molybdenum, and cobalt can be used in the present invention.

The conditions for culturing the microorganisms can be chosen from those which are preferable for their growth. For culturing microorganisms of the genus Thermoanaerobium, they are generally cultured under anaerobic conditions at temperatures of 50–80° C., preferably, 60–70° C., and at pHs of 5–8, preferably, 6.5–7.5. Any cultivation time can be used in the present invention as long as it is sufficient for the growth of the microorganisms used in the present invention, preferably, 10–50 hours. In the case of using the above transformants, they are usually cultured under aerobic conditions by aeration-agitation at temperatures of 20–65° C. and pHs of 2–9 for about 1–6 days, which are varied depending on the types of the transformants.

After culturing the microorganisms, the present enzyme can be collected from the cultures. Because the enzyme activity may be generally present intracellularly, intact and processed cells can be obtained as crude enzymes. Whole cultures can be also used as crude enzymes. Conventional solid-liquid separation methods can be used to separate cells and nutrient culture media; for example, methods to directly centrifuge the cultures, those to filtrate the cultures after adding filer aids to the cultures or after pre-coating, and those to filter the cultures using membranes such as plain filters and hollow fibers can be used. The intact and processed cells per se can be used as crude enzymes, and if necessary, they can be prepared into partially purified enzymes. In the case of transformants prepared with microorganisms of the genus Bacillus as hosts, the desired enzyme may be secreted in the nutrient culture media depending on the types of recombinant DNAs used for transformation. In such a case, the culture supernatants can be used as crude enzymes.

The types of the processed cells include protein fractions of cells, immobilized substances of the intact and processed cells, and cells which were dried, lyophilized, and treated with surfactants, enzymes, ultrasonication, mechanical grinding, and mechanical pressure. The present enzyme can be used in a crude or purified form, and the processed cells can be usually further treated with conventional methods used for purifying enzymes, for example, salting out using ammonium sulfate, sedimentation using acetone and alcohol, and membrane concentration/dialysis using plain membranes and hollow fibers.

The intact and processed cells can be immobilized by known methods; for example, binding methods with ion exchangers, covalent bonding/adsorption methods with resins and membranes, and inclusion methods using high molecular substances.

The crude enzymes can be used intact or may be purified by conventional purification methods. For example, the processed cells are salted out using ammonium sulfate into crude enzymes, followed by dialyzing the enzymes and treating them successively with anion exchange column chromatography using "DEAE-TOYOPEARL®", an anion exchanger commercialized by Tosoh Corporation, Tokyo, Japan, cation exchange column chromatography using "CM-TOYOPEARL®", a cation exchanger commercialized by Tosoh Corporation, Tokyo, Japan, hydrophobic column chromatography using "BUTYL-TOYOPEARL®", a hydrophobic exchanger commercialized by Tosoh Corporation, and gel filtration column chromatography using "ULTROGEL® AcA44 RESIN", a gel for gel filtration column chromatography commercialized by Sepracor/IBF s.a. Villeneuve la Garenne, France, to obtain an electrophoretically single protein band of enzyme.

The present kojibiose phosphorylase activity is assayed as follows: Add 0.2 ml of an enzyme solution to 2 ml of 20 mM McIlvaine buffer (pH 5.5) containing 1.0 w/v % kojibiose as a substrate, incubate the solution at 60° C. for 30 min, sample the reaction mixture in an amount of 0.5 ml, and incubate the sample at 100° C. for 10 min to suspend the enzymatic reaction. Add 0.5 ml of D-glucose oxidase/peroxidase reagent to the heated sample, stir the mixture, keep the mixture at 40° C. for 30 min, add 2.5 ml of 5-N hydrochloric acid, stir the resulting mixture, and measure the absorbance of the mixture at a wavelength of 525 nm. One unit of the enzyme activity is defined as the enzyme that forms one $\mu$mole of D-glucose per one minute. The activity of maltose- and trehalose-phosphorylases can be assayed similarly as the same assay as indicated above except that the kojibiose as a substrate is respectively replaced with maltose and trehalose.

In the present enzymatic reaction using the kojibiose phosphorylase to produce saccharide compositions containing glucosyl-transferred saccharides, the enzyme is generally allowed to contact with $\beta$-D-glucose-1-phosphoric acid as a saccharide donor under the following conditions along with other appropriate saccharides as acceptors, for example, monosaccharides such as D-glucose and L-sorbose, disaccharides such as maltose, kojibiose, trehalose, and sucrose, and tri- and higher-oligosaccharides such as maltotriose, maltotetraose, and maltopentaose. As a result, depending on the acceptors used, glucosyl-transferred saccharides including kojibiose, glucosylsorbose, kojibiosylglucose, kojitriose, kojibiosylglucoside, kojibiosylfructoside, kojibiosylmaltose, kojibiosylmaltotriose, and kojibiosyl-maltotetraose are formed. Among these glucosyl-transferred saccharides, glucosylsorbose and kojibiosefructoside are novel saccharides firstly found by the present invention.

Commercially available $\beta$-D-glucose-1-phosphoric acid as a reagent can be used intact as a saccharide donor in the present invention, and it can be prepared by contacting an appropriate phosphorylase with a saccharide as a substrate in the presence of an inorganic phosphoric acid and/or its salt; for example, it can be prepared by, in the presence of an inorganic phosphoric acid and/or its salt, contacting kojibiose phosphorylase with kojibiose, contacting maltose with maltose phosphorylase, or contacting trehalose with trehalose phosphorylase. When either of the above reactions of the phosphorylases, that form $\beta$-D-glucose-1-phosphoric acid, is conducted in the same reaction system using the present kojibiose phosphorylase to form glucosyl-transferred saccharides, it can directly supply $\beta$-D-glucose-1-phosphoric acid to the system, resulting in a reduction of the production costs and a simplification of the production steps as advantageous features. As described above, two or more types of saccharides as acceptors can be arbitrarily used at the same time. The inorganic phosphoric acid as mentioned above includes orthophosphoric acid and condensed phosphoric acid, and usually, the former acid is preferably used. The salt of inorganic phosphoric acid includes compounds of phosphoric ion in general, derived from the above inorganic phosphoric acid, and usually, highly-water soluble sodium- and potassium-salts of phosphoric acid are preferably used.

The substrate concentration used in the glucosyl-transferred saccharide formation reaction using the present kojibiose phosphorylase is not specifically restricted. Generally, preferably used are 1–20 w/w % aqueous solutions (the working "w/w %" will be abbreviated as "%" throughout the specification, unless specified otherwise) of β-D-glucose-1-phosphoric acid as a saccharide donor and 1–20% aqueous solutions containing acceptors. As described above, when the β-D-glucose-1-phosphoric acid formation reaction by an appropriate phosphorylase is conducted in the same reaction system of the above glucosyl-transferred saccharide-forming reaction, the followings are recommendable: When employing the action of kojibiose phosphorylase, about 1–20% aqueous solutions of kojibiose are used in place of β-D-glucose-1-phosphoric acid as the substrate of glucosyl-transferring reaction, while coexisting about 0.5–20 mM of phosphates such as sodium dihydrogenphosphate. When employing other phosphorylase, about 1–20% maltose or trehalose can be coexisted with about 0.5–20 mM of phosphates such as sodium dihydrogenphosphate in place of the β-D-glucose-1-phosphoric acid as a substrate for the glucosyl-transferring reaction, and depending on the saccharides used, maltose- or trehalose-phosphorylase can be preferably coexisted in an amount of about 0.1–50 units/g saccharide, on a dry solid basis (d.s.b.).

The above reaction can be carried out at temperatures that do not inactivate the enzymes used, i.e. up to about 70° C., preferably, about 15–65° C. The reaction pH can be usually adjusted to pHs of about 4.0–9.0, preferably, about 5.0–7.5. The reaction time can be appropriately chosen depending on the enzymatic reaction rates, usually, it is about 0.1–100 hours when the enzymes are used in an amount of about 0.1–50 units/g substrate, d.s.b. As described above, when the β-D-glucose-1-phosphoric acid formation reaction using other phosphorylases is conducted in the same reaction system of the glucosyl-transferred saccharide-forming reaction, the reaction temperatures and pHs are preferably set to those which do not inactivate the phosphorylases used depending on their thermal stabilities.

Thus, the resulting reaction mixtures contain glucosyl-transferred saccharides corresponding to the saccharides used as substrates. The yields of glucosyl-transferred saccharides differ depending on the substrate concentrations, types of substrates, and reaction conditions used in the enzymatic reactions. For example, in the case of using 5% β-D-glucose-1-phosphoric acid and 25% sorbose are used as substrates, glucosylsorbose is formed in a yield of about 30%. Throughout the specification, the yields of glucosyl-transferred saccharides means their percentages (%) of the formed saccharides to the total saccharides in reaction mixtures, d.s.b.

To increase the content of glucosyl-transferred saccharides in reaction mixtures, enzyme sources, which decompose and remove D-glucose formed in the reaction mixtures, can be advantageously coexisted in the mixtures to promote the saccharide-transferring reactions. Such a technique can be satisfactorily used to decompose and remove D-glucose as a by-product formed during the reaction processes and to promote the saccharide-transferring reaction when the above β-D-glucose-1-phosphoric acid formation reaction using an appropriate phosphorylase is carried out in the same reaction system of the glucosyl-transferring reaction to directly supply saccharide donors.

Enzyme sources having a D-glucose decomposing activity include microorganisms with such an activity, their cultures, cells, and processed cells, as well as enzymes with such an activity. Any microorganisms can be used as long as they have a relatively-high D-glucose decomposing activity but have no or substantially no activity of decomposing the formed transferred saccharides; preferable ones are yeasts. Any enzymes such as glucose oxidase, catalase, pyranose oxidase, glucose dehydrogenase, glucokinase, and kexokinase can be used. The glucose oxidase and catalase can be preferably used.

The reaction mixtures containing the glucosyl-transferred saccharides thus produced can be in a conventional manner filtered and centrifuged to remove impurities, then subjected to purification steps such as decoloration with activated charcoals, and desalting with ion exchangers in H- and OH-form, and concentrated into syrupy products. If necessary, the syrupy products can be arbitrarily dried by methods such as spray drying into powdery products.

The present saccharide compositions containing glucosyl-transferred saccharides can be processed into products rich in the saccharides by separating the saccharides from reaction mixtures and purifying the resulting mixtures. Examples of such separation methods are those which separate and remove impurities; fermentation methods using yeasts which remove monosaccharides by fermentations using yeasts, membrane filtrations, and column chromatographies. More particularly, it is advantageously used on an industrial scale a method for collecting fractions rich in the desired glucosyl-transferred saccharides by removing concomitant saccharides on a column chromatography using an alkaline strong-acid cation exchange resin as disclosed in Japanese Patent Kokai Nos. 23,799/83 and 72,598/83. In this case, conventional fixed-bed, moving-bed, and semi-moving methods can be arbitrarily used.

The solutions separated from impurities can be in a conventional manner filtered and centrifuged to remove insoluble substances, subjected to purification steps such as decoloration with activated charcoals, and desalting with ion exchange resins in H- and OH-form, and concentrated into syrupy products. If necessary, the syrupy products can be dried by methods such as spray drying into powdery products.

The present saccharide compositions containing glucosyl-transferred saccharides thus obtained usually contain at least 5%, preferably, at least 10% of the glucosyl-transferred saccharides, d.s.b.

The present saccharide compositions formed by the present kojibiose phosphorylase have a satisfactory taste and sweetness, osmosis-controlling ability, humectancy, gloss-imparting ability, crystallization-preventing ability, and retrogradation-preventing ability, anti-cariosity, growth-promoting activity for bifid bacteria, and mineral-absorption-promoting activity. Because of these satisfactory properties and functions, the present saccharide compositions can be arbitrarily used widely in compositions such as food products, tobaccos, cigarettes, feeds, pet foods, cosmetics, pharmaceuticals, shaped bodies, daily foods and products, products of forestry and fisheries, reagents, and products for chemical industries.

The present saccharide compositions containing glucosyl-transferred saccharides can be used intact as a seasoning for sweetening. If necessary, the present saccharide compositions can be used together with adequate amounts of one or more other sweeteners, for example, powdered syrup, glucose, maltose, trehalose, sucrose, isomerized sugar, honey, maple sugar, sorbitol, maltitol, lactitol, dihydrocharcone, stevioside, α-glycosyl stevioside, rebaudioside, glycyrrhizin, L-aspartyl-L-phenylalanine methyl ester, saccharin, glycine, and alanine, as well as fillers such as dextrins, starches, and lactose.

The present saccharide compositions have a sweetness which well harmonizes with substances having sourness, acidity, saltiness, bitterness, astringency, and deliciousness, as well as a satisfactory acid- and heat-tolerance. Thus, they can be arbitrarily used in food products in general as a sweetener, taste-improving agent, and quality-improving agent.

The present saccharide compositions can be used in seasonings such as soy sauces, powdered soy sauces, "miso", "funmatsu-miso" (a powdered miso), "moromi" (a refined sake), "hishio" (a refined soy sauce), "furikake" (a seasoned fish meal), mayonnaise, dressings, vinegars, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauces, catsups, premixes for pickles and pickled products such as "takuan-zuke-no-moto" (a premix for pickled radish), and "hakusai-zuke-no-moto" (a premix for fresh white rape pickles), "yakiniku-no-tare" (a sauce for Japanese grilled meat), curry roux, instant stew mixes, instant soup mixes, "dashi-no-moto" (an instant stock mix), mixed seasonings, "mirin" (a sweet sake), "shin-mirin" (a synthetic mirin), table syrups and coffee syrups.

The present saccharide composition can be freely used for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jellies, pao de Castellas and "amedama" (a Japanese toffee); confectioneries such as buns, biscuits, crackers, cookie, pies, puddings, butter creams, custard creams, cream puffs, waffles, sponge cakes, doughnuts, chocolates, chewing gums, caramels and candies; frozen desserts such as ice creams and sherbets; syrups such as "kajitsu-no-syrup-zuke" (a preserved fruit), and "korimitsu" (a sugar syrup for shaved ice); pastes such as flour pastes, peanut pastes, fruit pastes, and spreads; processed fruits and vegetables such as jams, marmalades, "syrup-zuke" (fruit pickles), and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); meat products such as hams and sausages; products of fish meats such as fish hams, fish sausages, "kamaboko" (a steamed fish paste), "chikuwa" (a kind of fish paste), and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-serume" (dried squid strips), and "fugu-no-mirin-boshi" (a dried mirin-seasoned swellfish); "tsukudani" (foods boiled down in soy sauce) such as those of lavers, edible wild plants, dried squids, fishes, and shell-fishes; daily dishes such as "nimame" (cooked beans), potato salads, and "konbu-maki" (a tangle roll); milk products; canned and bottled products such as those of meats, fish meats, fruits, and vegetables; alcoholic beverages such as synthetic sakes, wines and liquors; soft drinks such as coffees, teas, cocoas, juices, carbonated beverages, sour milk beverages, and beverages containing lactic acid bacteria; instant food products such as instant pudding mixes, instant hot cake mixes, and "sikuseki-shiruko" (an instant mix of adzuki-bean soup with rice cake), and instant soup mixes; and foods such as baby foods, foods for therapy, beverages supplemented with nutritions, peptide foods, frozen foods, cooked rice products, and noodles; as well as for improving the tastes and qualities of the above food products.

The present saccharide compositions can be also used in feeds and pet foods for animals such as domestic animals, poultry, honey bees, silk warms and fishes to improve their taste preferences. The present saccharide compositions can be arbitrarily used as a sweetener, taste-improving agent, quality-improving agent, and stabilizer in other products in a paste and liquid form such as tobaccos, cigarettes, dentifrices, lipstickes, rouges, lip creams, internal medicines, tablets, troches, cod liver oils in the form of drops, cachous, oral refrigerants, gargles, cosmetics, and pharmaceuticals.

The present saccharide compositions can be used as a quality-improving agent and stabilizer in biologically active substances susceptible to lose their effective ingredients and activities, as well as in health foods and pharmaceuticals containing the biologically active substances. Examples of such biologically active substances are solutions of cytokins such as $\alpha$-, $\beta$- and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor and interleukins 1, 2, 6, 15 and 18; hormones such as insulin, growth hormone, prolactin, erythropoietin, tissue plasminogen activator, follicle-stimulating hormone, and placental hormone; biological preparations such as BCG vaccine, Japanese encephalitis vaccine, measles vaccine, live polio vaccine, smallpox vaccine, tetanus toxoid, Trimeresurus antitoxin, and human immunoglobulin; antibiotics such as penicillin, erythromycin, chloramphenicol, tetracycline, streptomycin, and kanamycin sulfate; vitamins such as thiamine, riboflavin, L-ascorbic acid, cod liver oil, carotenoid, ergosterol, and tocopherol; enzymes such as lipase, elastase, urokinase, protease, $\beta$-amylase, isoamylase, glucanase, and lactase; extracts such as ginseng extract, snapping turtle extract, chlorella extract, aloe extract, and propolis extract; viable microorganisms such as viruses, lactic acid bacteria, and yeasts; and other biologically active substances such as royal jelly. By using the present saccharide compositions, the aforementioned biologically active substances are arbitrary prepared into health foods and pharmaceuticals with a satisfactorily-high stability and quality without fear of losing or inactivating their effective ingredients and activities.

As described above, the wording "compositions" as referred to in the present invention include orally- and parenterally-usable food products, cosmetics, and pharmaceuticals, as well as daily products, products of forestry and fisheries, reagents, and products for chemical industries.

Methods to incorporate the present saccharide compositions into the above compositions include conventional methods, for example, mixing, kneading, dissolving, melting, soaking, permeating, sprinkling, applying, coating, spraying, injecting, and solidifying. The present saccharide composition is usually incorporated into the compositions in an amount of 0.1% or more, preferably, 0.5% or more.

The following experiments explain the present invention in more detail:

EXPERIMENT 1

Preparation of Kojibiose Phosphorylase

According to the preparation of the medium for *Thermoanaerobium brockii* as disclosed in "ATCC Catalogue of BACTERIA AND BACTERIOPHAGES", 18th edition, pp. 452–456 (1992), except for replacing 0.5 w/v % glucose with 0.5 w/v % trehalose as a carbon source, a medium was prepared, and 100 ml aliquots of the medium were placed in 100-ml pressure bottles, followed by inoculating a seed culture of *Thermoanaerobium brockii*, ATCC 35047, and allowing to stand at 60° C. for 48 hours for a seed culture.

About 10 L aliquots of a fresh preparation of the same nutrient culture medium as used for preparing the seed culture were placed in four 11-l stainless steel bottles, sterilized by heating, cooled to 60° C., and inoculated with one v/v % of the seed culture to the culture medium, followed by the stationary culture at 60° C. for about 40 hours.

About 40 L of the resultant pooled cultures were centrifuged to obtain 92 g wet cells which were then suspended in 10 mM phosphate buffer, ultrasonicated, and centrifuged to obtain a supernatant of the disrupted cell suspension. The supernatant had an activity of 0.1 unit/ml of kojibiose phosphorylase.

EXPERIMENT 2

Purification of Kojibiose Phosphorylase

The supernatant in Experiment 1 was concentrated with a UF membrane into an about 360 ml of enzyme concentrate having an activity of about 10 units/ml of kojibiose phosphorylase.

Three hundred ml of the enzyme concentrate was dialyzed against 10 mM phosphate buffer (pH 7.0) for 24 hours, and centrifuged to remove insoluble substances. Three hundred and eighty ml of the resulting supernatant was subjected to ion exchange column chromatography using 380 ml of "DEAE-TOYOPEARL® 650 GEL", a gel for ion exchange column chromatography commercialized by Tosoh Corporation, Tokyo, Japan.

The present kojibiose phosphorylase was allowed to adsorb on the gel, and eluted from the column by feeding a linear gradient of sodium chloride increasing from 0 M to 0.5 M. Fractions with the enzyme activity, eluted at about 0.2 M sodium chloride, were collected and pooled, and the enzyme in the pooled solution was then purified by the following steps; Dialyze the solution against a fresh preparation of the same buffer containing 1.5 M ammonium sulfate, centrifuge the dialyzed solution to remove insoluble substances, and subjected the supernatant to hydrophobic column chromatography using 100 ml of "BUTYL-TOYOPEARL® 650 GEL". Elute the kojibiose phosphorylase adsorbed on the gel with a linear gradient of ammonium sulfate decreasing from 1.5 M to 0 M, and collect fractions with the enzyme activity.

The fractions were pooled and subjected to gel filtration chromatography sing 300 ml of "ULTROGEL® AcA44 RESIN", a gel for gel filtration column chromatography commercialized by Sepracor/IBS s.a. Villeneuve la Garenne, France, followed by collecting fractions with the enzyme activity.

The yield of the purified enzyme specimen, obtained by the above purification steps, was about 20% with respect to enzyme activity of the supernatant of the disrupted cell suspension. The enzyme specimen had a specific activity of 71.4 units/mg protein. Protein was quantified according to the Lowry method using calf serum albumin as a standard protein.

Examination for the purity of the specimen on gel electrophoresis using 7.5 w/v % polyacrylamide revealed that the specimen was a relatively-high purity protein detected as a single protein band.

EXPERIMENT 3

Property of Kojibiose Phosphorylase

The kojibiose phosphorylase specimen in Experiment 2 was subjected to SDS-PAGE using 10 w/v % gel. Comparing with marker proteins, commercialized by Japan Bio-Rad Laboratories, Tokyo, Japan, which were electrophoresed in parallel, the molecular weight of the enzyme was measured, revealing that it had a molecular weight of 83,000±5,000 daltons and gave a molecular weight of 5,000±30,000 daltons on gel filtration using a column, 7.5 mm in diameter and 600 mm in length, packed with "TSKgel G4000SW", a gel for gel filtration commercialized by Tosoh Corporation, Tokyo, Japan.

The purified kojibiose phosphorylase was subjected to polyacrylamide gel electrophoresis using 2 w/v % "AMPHOLINE", an ampholyte commercialized by Pharmacia LKB Biotechnology AB, Uppsala, Sweden, followed by measuring the pHs of protein bands and gels and revealing that the enzyme had a pI of 4.4±0.5.

Figure 2:
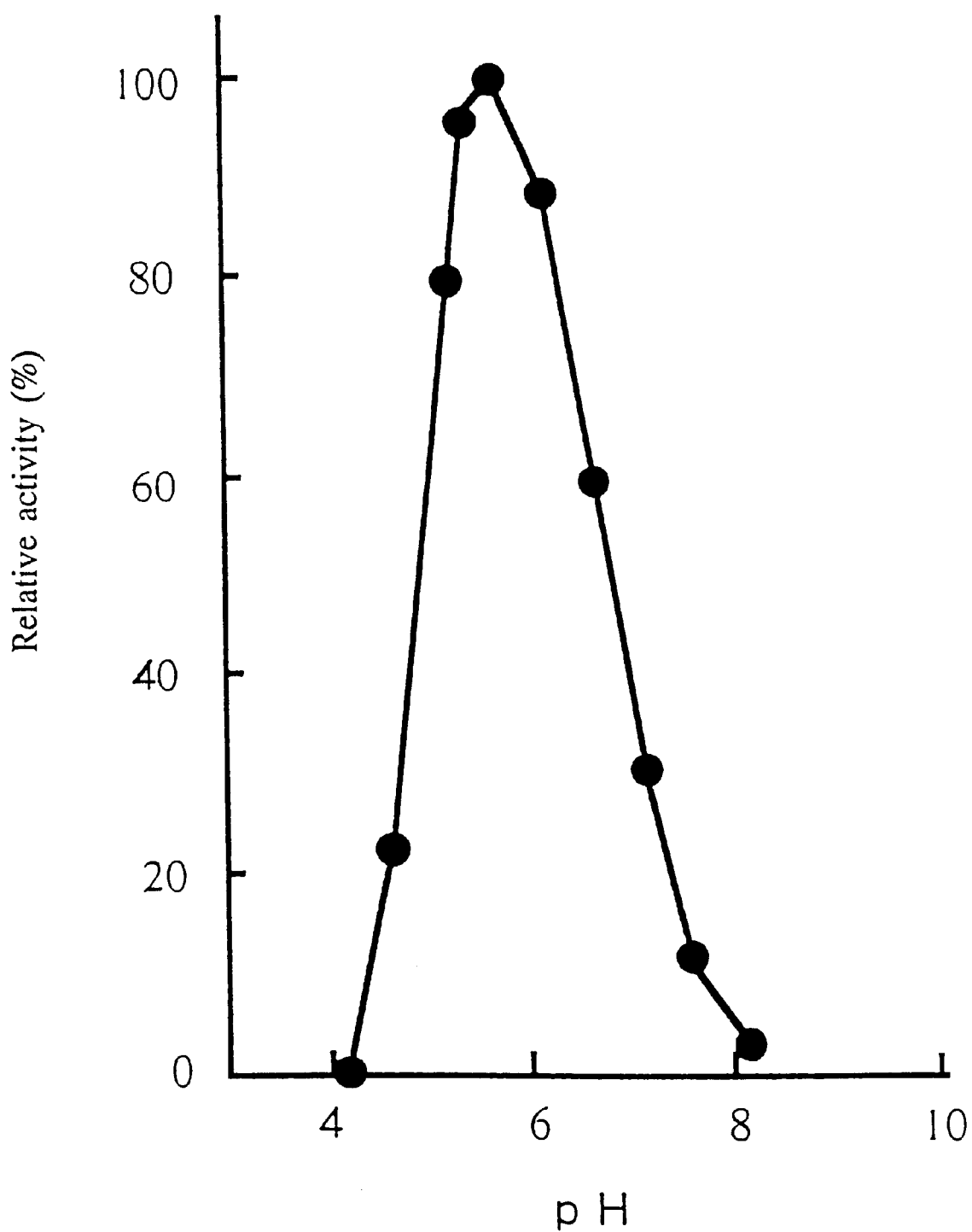
FIG. 2 shows the influence of pHs on the activity of kojibiose phosphorylase according to the present invention.
Figure 3:
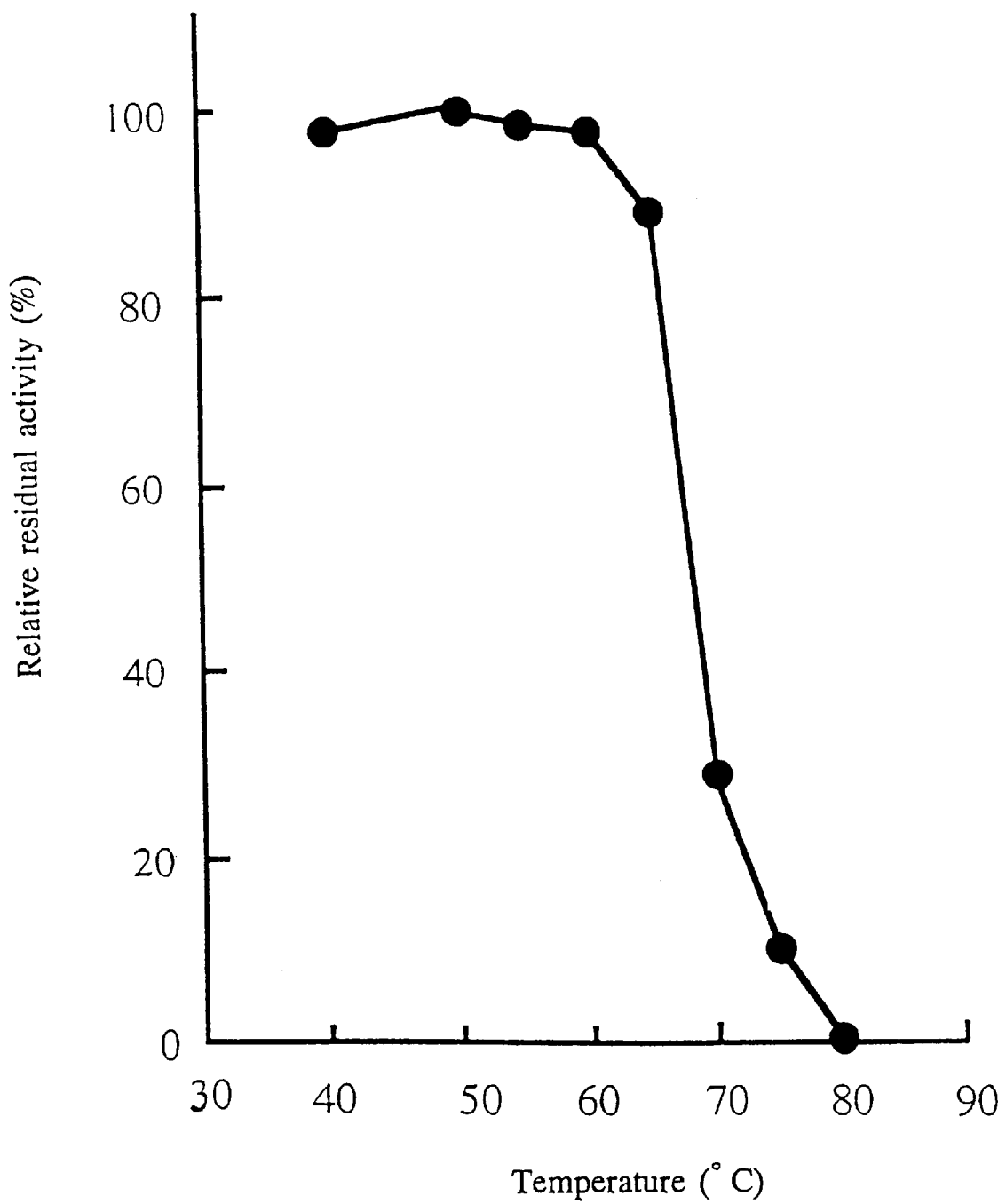
FIG. 3 shows the influence of temperatures on the stability of kojibiose phosphorylase according to the present invention.
Figure 4:
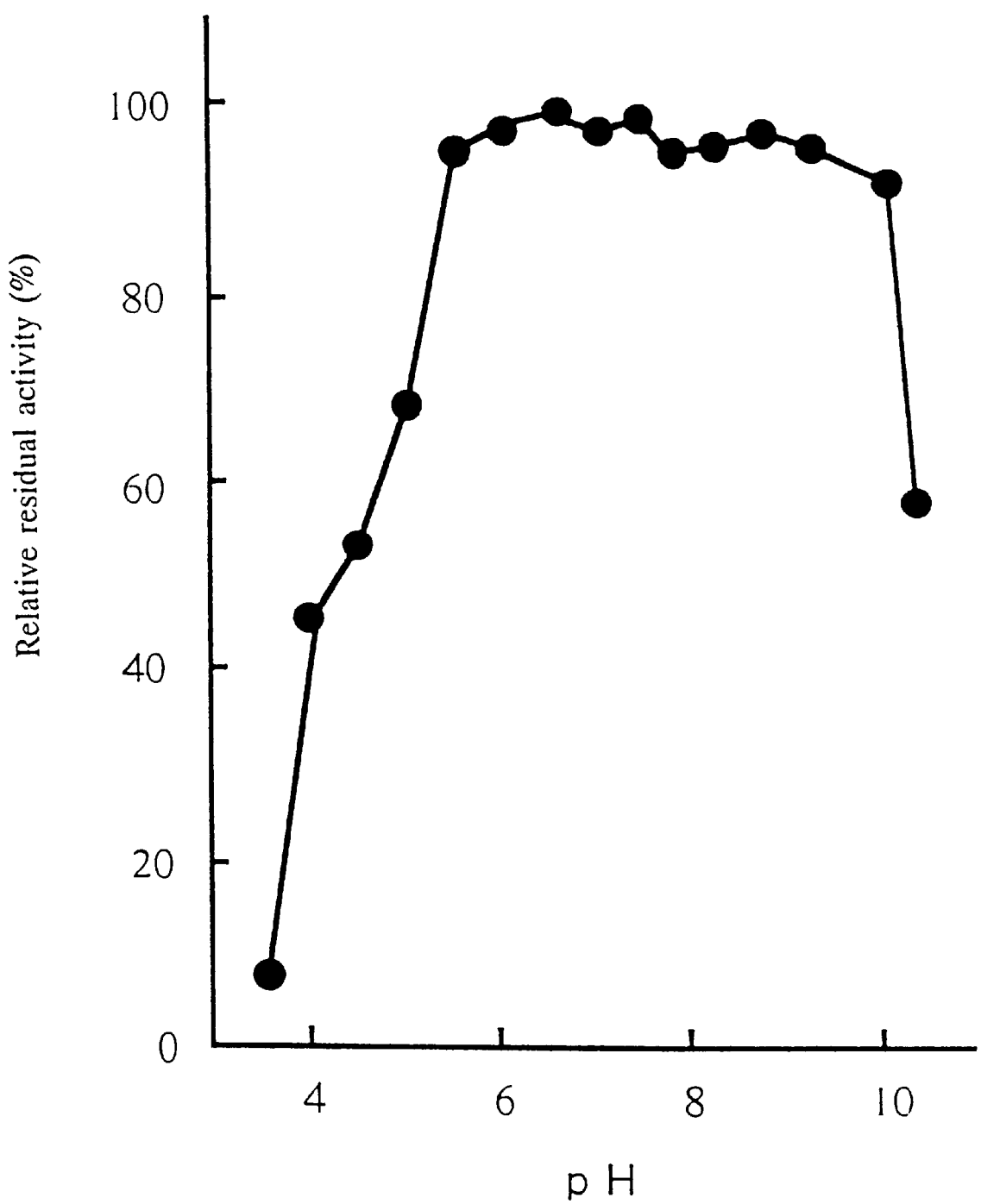
FIG. 4 shows the influence of pHs on the stability of kojibiose phosphorylase according to the present invention.

Influences of temperatures and pHs on the present kojibiose phosphorylase activity were studied in accordance with the assay for enzyme activity. To study the influence of temperature, the enzyme was reacted at temperatures of about 40–80° C. in place of 60° C. as used in the enzyme assay. In the case of studying the influence of pH, the enzyme was reacted at pHs of about 4–8 in place of the buffer's pH as used in the assay for the enzyme activity. In both cases, the enzymatic reactions were suspended similarly as in the enzyme assay, followed by quantifying the formed glucose. These results were in FIGS. 1 and 2 which were respectively the data for influences of temperatures and pHs, and expressed by relative values to the maxima. The enzyme had an optimum temperature of about 65° C. when incubated at pH 5.5 for 30 min, and the optimum pH was about 5.5 when incubated at 60° C. for 30 min. The thermal stability of the enzyme was determined by incubating the enzyme dissolved in 10 mM McIlvaine buffer (pH 5.5) at about 40–80° C. for one hour, cooling the incubated enzyme, and assaying for the residual enzyme activity according to the enzyme assay. The pH stability of the enzyme was determined by dissolving the enzyme in buffers with different pHs of about 3.5–10, keeping each enzyme solution at 4° C. for 24 hours, adjusting each solution to give a pH of 5.5, and assaying for the residual enzyme activity according to the enzyme assay. These results were in FIGS. 3 and 4 which were respectively the data for thermal and pH stabilities of the enzyme and expressed by relative values to the maxima. The enzyme had a thermal stability of up to about 65° C. and a pH stability of about 5.5–10.0. The enzyme activity was inhibited by one mM $Hg^{++}$.

EXPERIMENT 4

Partial Amino Acid Sequence of Kojibiose Phosphorylase

Experiment 4-(1)

N-Terminal Amino Acid Sequence

A portion of a purified enzyme specimen, obtained by the method in Experiment 2, was dialyzed against distilled water, and about 40 µg of the dialyzed enzyme as a protein was used as a sample for the analysis of N-terminal amino acid sequence. "PROTEIN SEQUENCER MODEL 473A", an apparatus commercialized by Applied Biosystems, Inc., Foster City, USA, was used to analyze up to five amino acid resides from the N-terminus. The analyzed partial amino acid sequence was SEQ ID NO: 1. More precise analysis using a fresh preparation of the same enzyme specimen revealed that the enzyme has the amino acid sequence of SEQ ID NO: 6 at the N-terminus.

Experiment 4-(2)

Internal Partial Amino Acid Sequence

A portion of a purified enzyme specimen, obtained by the method in Experiment 2, was dialyzed against 10 mM Tris-HCl buffer (pH 9.0), and the dialyzed solution was diluted with a fresh preparation of the same buffer to give a protein concentration of one mg/ml. One ml of the resulting solution was admixed with 10 μg of lysyl endopeptidase, an enzyme specimen commercialized by Wako Pure Chemical Industries, Ltd., Tokyo, Japan, and subjected to an enzymatic reaction at 30° C. for 22 hours to form peptides. Reversed phase HPLC (high-performance liquid chromatography) was performed to isolate the peptides under the conditions of: "μBONDASPHERE C-18 COLUMN (2.1 mm in diameter and 150 mm in length)", a column for HPLC commercialized by Waters Chromatography, Div., MILLIPORE Corp., Milford, Mass., USA, flow rate of 0.9 ml/min, ambient temperature, and a linear gradient of acetonitrile increasing from 0 v/v % to 48 v/v % in 0.1 v/v % trifluoroacetic acid over 120 min. Peptides eluted from the column were detected by measuring their absorbances at 210 nm. Two peptides, i.e., KP15 with a retention time of 66 min and KP23 with a retention time of 96 min, which were clearly separated from others, were separately collected, dried in vacuo, and dissolved in 200 μl of a solution of 0.1 v/v % trifluoroacetic acid and 50 v/v % acetonitrile. Each peptide was analyzed on a protein sequencer to reveal up to five amino acid residues from the N-terminus. The KP15 and KP23 gave the amino acid sequences of SEQ ID NO: 2 and SEQ ID NO: 3, respectively. More precise analysis of a fresh preparation of the same enzyme specimen by the same analysis revealed that the KP15 has SEQ ID NO: 7 at the N-terminus and the KP23 has SEQ ID NO: 8 at their N-termini.

EXPERIMENT 5

Substrate Specificity for Saccharide-Hydrolyzing Reaction by Kojibiose Phosphorylase An aqueous solution containing a saccharide selected from D-glucose, maltose, sucrose, lactose, trehalose, neotrehalose, cellobiose, melibiose, kojibiose, isomaltose, sophorose, gentibiose, nigerose, and laminaribiose was mixed with 10 units/g saccharide, d.s.b., of a purified kojibiose phosphorylase obtained by the method in Experiment 2, and incubated in the presence of 5 mM sodium dihydrogenphosphate at 60° C. and pH 5.5 for 24 hours.

The saccharide concentration of each reaction solution was 2 w/v %. Pre-reaction solutions and post-reaction mixtures were subjected to thin layer chromatography (hereinafter abbreviated as "TLC") using "KIESELGEL 60 (20×20 cm)", an aluminum plate for TLC commercialized by Merck & Co., Inc., Rahway, USA. Samples were developed once at ambient temperature on the plate using 1-butanol/pyridine/water (=7:3:1 by volume) as a developing solvent system, and the plate was sprayed with 20 v/v % sulfuric acid/methanol solution, and heated at 110° C. for about 10 min for coloration. Comparing spots of the solutions and mixtures detected on the plates, it was checked whether the enzyme acted on the saccharides. The results ere in Table 1:

TABLE 1

| Substrate | Decomposition |
| --- | --- |
| D-Glucose | – |
| Maltose | – |
| Sucrose | – |
| Trehalose | – |
| Neotrehalose | – |
| Cellobiose | – |
| Melibiose | – |
| Kojibiose | + |
| Isomaltose | – |
| Sophorose | – |
| Gentibiose | – |
| Nigerose | – |
| Laminaribiose | – |

Note)
+: Hydrolyzed by the action of kojibiose phosphorylase.
–: Not hydrolyzed by the action of kojibiose phosphorylase.

As shown in Table 1, it was found that the present kojibiose phosphorylase showed a strong substrate specificity to kojibiose and acted on it to form D-glucose and β-D-glucose-1-phosphoric acid, but did not act on other saccharides.

EXPERIMENT 6

Specificity to Acceptor in Glucosyl-Transferring Saccharide-Forming Reaction by Kojibiose Phosphorylase An aqueous solution, which dissolved in an equal amount by dry weight of β-D-glucose-1-phosphoric acid as a saccharide donor and one of the monosaccharides, oligosaccharides, and sugar alcohols as acceptors in Table 2, was admixed with 10 units/g β-D-glucose-1-phosphoric acid of a purified kojibiose phosphorylase obtained by the method in Experiment 2, and enzymatically reacted at 60° C. and pH 5.5 for 24 hours. The concentrations of the acceptors and the saccharide donors were adjusted to one w/v %. Similarly as in Experiment 5, the pre-reaction solutions and the post reaction mixtures were subjected to TLC, followed by coloring the plates. Comparing spots of the samples of the solutions and mixtures detected on the plates, it was judged whether transferred saccharides were formed based on newly detected spots of the post reaction mixtures. By macroscopically observing the coloration degree of the newly detected spots, the yield of the transferred saccharides was relatively evaluated. The results were in Table 2:

TABLE 2

| Acceptor | | Formation of glucosyl- |
| --- | --- | --- |
| Classification | Name | transferred saccharide |
| Aldopentose | D-Xylose | + |
| | L-Xylose | + |
| | D-Arabinose | – |
| | L-Arabinose | – |
| | D-Ribose | – |
| Aldohexose | D-Galactose | – |
| | D-Glucose | +++ |
| | D-Mannose | – |
| Ketohexose | L-Sorbose | +++ |
| | D-Fructose | – |
| Deoxysugar | 2-Deoxyglucose | – |
| | D-Fucose | + |
| | L-Fucose | + |
| | L-Rhamnose | – |

TABLE 2-continued

| | Acceptor | Formation of glucosyl- |
|---|---|---|
| Classification | Name | transferred saccharide |
| Glucoside | α-Methyl glucoside | +++ |
| | β-Methyl glucoside | +++ |
| Sugar alcohol | Sorbitol | – |
| Amino sugar | Glucosamine | – |
| | N-Acetyl glucosamine | – |
| Oligosaccharide | Maltose | +++ |
| | Isomaltose | +++ |
| | Kojibiose | +++ |
| | Laminaribiose | +++ |
| | Nigerose | +++ |
| | Cellobiose | ++ |
| | Gentibiose | ++ |
| | Trehalose | +++ |
| | Neotrehalose | +++ |
| | Sucrose | ++ |
| | Palatinose | +++ |
| | Maltulose | +++ |
| | Turanose | +++ |
| | Lactose | – |
| | Melibiose | – |
| | Lactulose | – |
| | Maltitol | +++ |
| | Maltotriose | +++ |
| | Maltotetraose | +++ |
| | Maltopentaose | +++ |

Note)
–: Glucosyl-transferred saccharide was not formed.
+: Glucosyl-transferred saccharide was formed in a relatively-small amount.
++: Glucosyl-transferred saccharide was formed in a relatively-large amount.
+++: Glucosyl-transferred saccharide was formed in an extremely-large amount.

As shown in Table 2, it was revealed that the present kojibiose phosphorylase effectively transferred glucosyl group from β-D-glucose-1-phosphoric acid as a saccharide donor to monosaccharides such as D-glucose and L-sorbose, disaccharides such as maltose, kojibiose, trehalose, and sucrose, and tri- and higher-oligosaccharides such as maltotriose, maltotetraose, and maltopentaose to form glucosyl-transferred saccharides. No glucosyl-transferred saccharide was formed when α-D-glucose-1-phosphoric acid was used in place of the β-D-glucose-1-phosphoric acid.

Some of the glucosyl-transferred saccharides, which were revealed in Experiment 6 to be formed via the saccharide-transferring reaction by the present kojibiose phosphorylase, well be explained in detail with reference to the following Experiments 7 to 12.

EXPERIMENT 7

Glucosyl-Transferred Saccharide from D-glucose and β-D-glucose-1-phosphoric Acid The saccharide component of the enzymatic reaction mixture, obtained in Experiment 6 using as substrates D-glucose and β-D-glucose-1-phosphoric acid, was analyzed on gas chromatography (hereinafter abbreviated as "GLC"). A portion of the reaction mixture was dried up, dissolved in pyridine, and trimethylsilylated for a sample for GLC analysis using a stainless steel column, 3 mm in diameter and 2 m in length, packed with 2% "SILICONE OV-17/CHROMOSOLB W", a resin for GLC commercialized by GL Sciences Inc., Tokyo, Japan. The conditions used for GLC were as follows: nitrogen gas as a carrier gas, flow rate of 40 ml/min, column oven temperatures of 160–320° C., and heating-up rate of 7.5° C./min. Saccharide components were detected by a hydrogen flame ionization detector.

As a result, the retention time of a peak for a glucosyl-transferred saccharide formed from D-glucose and β-D-glucose-1-phosphoric acid by the action of the present kojibiose phosphorylase was agreed with that of authentic kojibiose. Based on this, it was estimated that the glucosyl-transferred saccharide was kojibiose.

EXPERIMENT 8

Glucosylsorbose

To identify the glucosyl-transferred saccharide formed via the saccharide-transferring reaction to L-sorbose by the present kojibiose phosphorylase, the saccharide was prepared, isolated, and examined for structure; provide an aqueous solution containing 2.5% β-D-glucose-1-phosphoric acid and 2.5% L-sorbose, adjust the aqueous solution to give a pH of 5.0, add to the solution 10 units/g β-D-glucose-1-phosphoric acid of a purified kojibiose phosphorylase obtained by the method in Experiment 2, react the solution at 60° C. for 48 hours, heat the reaction mixture at 100° C. for 10 min to inactivate the remaining enzyme, and analyze on GLC a sample from the resulting mixture obtained according to the method in Experiment 7. As a result, it was confirmed that the reaction mixture contained a relatively-large amount of a substance with a retention time differing from those of L-sorbose and β-D-glucose-phosphoric acid, and that it was estimated to be the glucosyl-transferred saccharide. Based on the data from GLC, the yield of the saccharide was about 24%. The remaining reaction mixture was decolored with activated charcoals, filtered, desalted and purified using ion exchange resins in H- and OH-form, concentrated up to give a concentration of about 50%, and subjected to the column chromatography below, followed by collecting fractions rich in the glucosyl-transferred saccharide.

The resin used for fractionation was "XT-1016", and alkali metal strong-acid cation exchange resin, Na-form, polymerization degree of 4%, commercialized by Tokyo Organic Chemical Industries, Ltd., Tokyo, Japan, and the resin was suspended in water, packed in four jacketed-stainless steel columns, 3 cm in diameter and one m in length each, which were cascaded in series to give a total gel-bed depth of about 4 m. Keeping the inner column temperature at 40° C., a saccharide solution was fed to the columns in a volume of 5 v/v % to the resin, followed by feeding to the columns water heated to 40° C. at a flow rate of SV (space velocity) 0.15 to fractionate the saccharide solution and collecting fractions rich in the glucosyl-transferred saccharide.

The fractions were pooled, desalted, purified, and concentrated into an about 40% concentrate which was then chromatographed on a column packed with "YMC-Pack OSD", an octadecyl silica gel commercialized by YMC Co., Ltd., Kyoto, Japan, to collect fractions containing the glucosyl-transferred saccharide. The fractions were pooled and concentrated into an about 40% concentrate which was then re-applied to the above column chromatography. The resulting solution rich in the glucosyl-transferred saccharide was desalted, purified, concentrated, and dried in vacuo to obtain a powdery product containing the saccharide in a yield of about 20%, d.s.b., to the material saccharide used in the enzymatic reaction. In accordance with the method in Experiment 7, the powdery product was analyzed on GLC, revealing that it contained about 98% of the glucosyl-transferred saccharide, d.s.b.

The powdery product rich in the glucosyl-transferred saccharide was subjected to GLC analysis after decomposed with acids, revealing that the saccharide produced D-glucose and L-sorbose in a molar ratio of about 1:1 when decomposed with acids. The powdery product was methylated, hydrolyzed by acids, reduced, and acetylated to obtain partial methylhexytolacetate which was then analyzed on GLC to detect 2,3,4,6-tetramethyl-1,5-diacetylglucitol. Based on these, the glucosyl-transferred saccharide is composed of D-glucose and L-sorbose in a molar ratio of 1:1 where the OH-group at C-1 of D-glucose relates to the bonding between these saccharides. It can be estimated that a methyl derivative of sorbose was not detected due to the decomposition with acids.

To examine the structure of the glucosyl-transferred saccharide in more detail, the saccharide was measured for $^{13}$C-NMR spectrum. As a result, it gave $^{13}$C-NMR spectra (100 MHz, $D_2O$): σppm from TSP of 101.2, 100.4, 99.5, 99.3, 77.1, 75.6, 74.9, 74.5, 74.0, 73.2, 72.2, 66.3, 63.2, and 62.1. Based on the data, the glucosyl-transferred saccharide was identified as glucosylsorbose as a disaccharide, i.e., α-D-glucosyl-(1→5)-L-sorbose, composed of D-glucose and L-sorbose which links together via an α-bonding at C-1 of D-glucose and C-5 of L-sorbose. The compound was a novel saccharide.

EXPERIMENT 9

Kojibiosylglucose

To confirm a glucosyl-transferred saccharide formed by the transferring reaction of D-glucose to maltose by the present kojibiose phosphorylase, the glucosyl-transferred saccharide was prepared, isolated, and examined for structure as follows: An aqueous solution containing 5% β-D-glucose-1-phosphoric acid and 10% maltose was adjusted to give a pH of 6.0, and mixed with 20 units/g β-D-glucose-1-phosphoric acid, d.s.b., of a purified kojibiose phosphorylase obtained by the method in Experiment 2, followed by an enzymatic reaction at 60° C. for 48 hours. Thereafter, the reaction mixture was heated at 100° C. for 10 min to inactivate the remaining enzyme. In accordance with the method in Experiment 7, a portion of the reaction mixture was analyzed on GLC. As a result, it was confirmed that the reaction mixture contained a relatively-large amount of a compound with a retention time differing from those of maltose and β-D-glucose-1-phosphoric acid, resulting in a conclusion of that the compound was the glucosyl-transferred saccharide. The yield was about 40%, d.s.b., from the data on GLC. Similarly as in Experiment 8, the remaining reaction mixture was fractionated, purified, concentrated, and dried in vacuo to obtain a powdery product rich in the glucosyl-transferred saccharide in a yield of about 20% to the material saccharide, d.s.b. The powdery product contained about 98% of the glucosyl-transferred saccharide, d.s.b.

The powdery product was methylated, hydrolyzed by acids, reduced, and acetylated to obtain a partial methylhexytolacetate which was then subjected to GLC analysis. The analysis detected 2,3,4,6-tetramethyl-1,5-diacetylglucitol, 3,4,6-trimethyl-1,2,5-triacetylglucitol, and 2,3,6-trimethyl-1,4,5-triacetylglucitol, in a molar ratio of about 1:1:1. The data indicates that the glucosyl-transferred saccharide is an oligosaccharide composed of glucose molecules; one with a bonding-related OH-group at C-1, the other with either bonding-related OH-groups at C-1 and C-2 or a bonding-related OH-group at C-2, and the other with either bonding-related OH-groups at C-1 and C-4 or a bonding-related OH-group at C-4, in a molar ratio of 1:1:1.

To examine the structure of the glucosyl-transferred saccharide in more detail, the saccharide was measured for $^{13}$C-NMR spectrum. As a result, it gave $^{13}$C-NMR spectra (100 MHz, $D_2O$): σppm from TSP of 99.5, 99.4, 99.1, 98.6, 94.6, 79.2, 78.8, 78.6, 78.0, 77.6, 77.3, 77.0, 76.1, 75.6, 75.3, 74.7, 74.2, 74.1, 73.8, 72.7, 72.2, 72.1, 63.6, 63.5, 63.2, and 63.1. Based on the data, the glucosyl-transferred saccharide was identified as kojibiosylglucose, a trisaccharide, i.e., α-D-glucosyl-(1→2)-α-D-glucosyl-(1→4)-D-glucose, composed of maltose and D-glucose which links to the glucose residue at the non-reducing end of maltose via an α-1,2 linkage.

EXPERIMENT 10

Kojotriose

To confirm the glucosyl-transferred saccharide formed by the transferring reaction of D-glucose to kojibiose by the present kojibiose phosphorylase, the glucosyl-transferred saccharide was prepared, isolated, and examined for structure as follows: Five mM of sodium dihydrogenphosphate containing 20% kojibiose was adjusted to give a pH of 5.5, and mixed with 10 units/g kojibiose, d.s.b., of a purified kojibiose phosphorylase obtained by the method in Experiment 2, followed by an ezymatic reaction at 60° C. for 48 hours. Thereafter, the reaction mixture was heated at 100° C. for 10 min to inactivate the remaining enzyme. In accordance with the method in Experiment 7, a portion of the reaction mixture was analyzed on GLC. As a result, it was confirmed that the reaction mixture contained kojibiose and a relatively-large quantity of a compound with a retention time differing from those of D-glucose and β-D-glucose-1-phosphoric acid, resulting in a conclusion of that the compound was the glucosyl-transferred saccharide. The yield was about 30%, d.s.b., from the data on GLC. Similarly as in Experiment 8, the remaining reaction mixture was fractionated, purified, concentrated, and dried in vacuo to obtain a powdery product rich in the glucosyl-transferred saccharide in a yield of about 15% to the material kojibiose, d.s.b. The powdery product contained about 98% of the glucosyl-transferred saccharide, d.s.b.

The powdery product was methylated, hydrolyzed by acids, reduced, and acetylated to obtain a partial methylhexytolacetate which was then subjected to GLC analysis. The analysis detected 2,3,4,6-tetramethyl-1,5-diacetylglucitol and 3,4,6-trimethyl-1,2,5-triacetylglucitol in a molar ratio of about 1:2. The data strongly indicates that the glucosyl-transferred saccharide is an oligosaccharide composed of glucose molecules; one with a bonding-related OH-group at C-1, the other with bonding-related OH-groups at C-1 and C-2, and the other with a bonding-related OH-group at C-2, in a molar ratio of 1:1:1.

To examine the structure of the glucosyl-transferred saccharide in more detail, the saccharide was measured for $^{13}$C-NMR spectrum. As a result, it gave $^{13}$C-NMR spectra (100 MHz, $D_2O$): σppm from TSP of 99.3, 99.0, 98.3, 97.6, 96.5, 92.2, 81.3, 78.8, 78.6, 78.5, 77.2, 77.1, 75.7, 75.6, 74.7, 74.6, 74.5, 74.3, 74.2, 74.1, 74.0, 73.9, 72.6, 72.3, 72.2, 72.1, 72.0, 63.6, 63.4, 63.2, 63.1, 63.1, and 63.0. Based on the data, the glucosylkojibiose was identified as kojitriose, a trisaccharide, i.e., α-D-glucosyl-(1→2)-α-D-glucosyl-(1→2)-D-glucose, composed of kojibiose and D-glucose which links to the glucose residue at the non-reducing end of kojibiose via an α-1,2 linkage.

EXPERIMENT 11

Kojibiosylglucoside

To confirm a glucosyl-transferred saccharide formed by the transferring reaction of D-glucose to trehalose by the present kojibiose phosphorylase, the glucosyl-transferred saccharide was prepared, isolated, and examined for structure as follows: An aqueous solution containing 5% β-D-glucose-1-phosphoric acid and 10% trehalose was adjusted to give a pH of 5.5, and mixed with 10 units/g β-D-glucose-1-phosphoric acid, d.s.b., of a purified kojibiose phosphorylase obtained by the method in Experiment 2, followed by an enzymatic reaction at 60° C. for 48 hours. Thereafter, the reaction mixture was heated at 100° C. for 10 min to inactivate the remaining enzyme. In accordance with the method in Experiment 7, a portion of the reaction mixture was analyzed on GLC. As a result, it was confirmed that the reaction mixture contained a relatively-large amount of a compound with a retention time differing from those of β-D-glucose and trehalose, resulting in a conclusion of that the compound was the glucosyl-transferred saccharide. The yield was about 75%, d.s.b., from the data on GLC. Similarly as in Experiment 8, the remaining reaction mixture was fractionated, purified, concentrated, and dried in vacuo to obtain a powdery product rich in the glucosyl-transferred saccharide in a yield of about 65% to the material saccharide, d.s.b. The powdery product contained about 98% of the glucosyl-transferred saccharide, d.s.b.

The powdery product was methylated, hydrolyzed by acids, reduced, and acetylated to obtain a partial methylhexytolacetate which was then subjected to GLC analysis. The analysis detected 2,3,4,6-tetramethyl-1,5-diacetylglucitol and 3,4,6-trimethyl-1,2,5-triacetylglucitol in a molar ratio of about 2:1. The data indicates that the glucosyl-transferred saccharide is an oligosaccharide composed of glucose molecules; one with a bonding-related OH-group at C-1, and the other with a bonding-related OH-groups at C-1 and C-2, in a molar ratio of 2:1.

To examine the structure of the glucosyl-transferred saccharide in more detail, the saccharide was measured for $^{13}$C-NMR spectrum. As a result, it gave $^{13}$C-NMR spectra (100 MHz, $D_2O$): σppm from TSP of 98.6, 96.2, 93.3, 77.3, 75.8, 75.4, 75.1, 74.8, 74.6, 74.6, 74.0, 73.9, 72.5, 72.3, 72.2, 63.4, 63.4, and 63.3. Based on the data, the glucosyltrehalose was identified as kojibiosylglucoside or selaginose, a trisaccharide, i.e., α-D-glucosyl-(1→2)-α-D-glucosyl-(1,1)-α-D-glucoside, composed of trehalose and D-glucose which links to the glucose residue at the non-reducing end of trehalose via an α-1,2 linkage.

EXPERIMENT 12

Kojibiosylfructoside

To confirm a glucosyl-transferred saccharide formed by the transferring reaction of D-glucose to sucrose by the present kojibiose phosphorylase, the glucosyl-transferred saccharide was prepared, isolated, and examined for structure as follows: An aqueous solution containing 5% β-D-glucose-1-phosphoric acid and 10% sucrose was adjusted to give a pH of 5.5, and mixed with 10 units/g β-D-glucose-1-phosphoric acid, d.s.b., of a purified kojibiose phosphorylase obtained by the method in Experiment 2, followed by an enzymatic reaction at 60° C. for 48 hours. Thereafter, the reaction mixture was heated at 100° C. for 10 min to inactivate the remaining enzyme. In accordance with the method in Experiment 7, a portion of the reaction mixture was analyzed on GLC. As a result, it was confirmed that the reaction mixture contained a relatively-large amount of a compound with a retention time differing from those of β-D-glucose-1-phosphoric acid and sucrose, resulting in a conclusion of that the compound was the glucosyl-transferred saccharide. The yield was about 70%, d.s.b., from the data on GLC. Similarly as in Experiment 8, the remaining reaction mixture was fractionated, purified, concentrated, and dried in vacuo to obtain a powdery product rich in the glucosyl-transferred saccharide in a yield of about 50% to the material saccharide, d.s.b. The powdery product contained about 98% of the glucosyl-transferred saccharide, d.s.b.

The powdery product was hydrolyzed by acids and subjected to GLC analysis, revealing that it formed D-glucose and D-fructose in a molar ratio of about 2:1. The powdery product was methylated, hydrolyzed by acids, reduced, and acetylated to obtain a partial methylhexytolacetate. The GLC analysis detected 2,3,4,6-tetramethyl-1,5-diacetylglucitol and 3,4,6-trimethyl-1,2,5-triacetylglucitol in a molar ratio of 1:1. These data indicate that the glucosyl-transferred saccharide is composed of D-glucose and D-fructose in a molar ratio of 2:1, and that one of the D-glucose molecules has a bonding-related OH-group at C-1, and the other has a bonding-related OH-groups at C-1 and C-2, in a molar ratio of 1:1. It can be speculated that no methyl derivative of D-fructose was found due to the acid decomposition.

To examine the structure of the glucosyl-transferred saccharide in more detail, the saccharide was measured for $^{13}$C-NMR spectrum. As a result, it gave $^{13}$C-NMR spectra (100 MHz, $D_2O$): σppm from TSP of 107.0, 99.3, 92.5, 84.0, 79.1, 78.5, 76.5, 75.7, 74.9, 74.7, 74.1, 74.0, 72.2, 72.1, 64.9, 64.6, 63.2, and 63.1. Based on the data, the glucosylsucrose was identified as kojibiosylfructoside, a trisaccharide, i.e., α-D-glucosyl-(1→2)-α-D-glucosyl-(1→2)-β-D-fructoside, composed of sucrose and D-glucose which links to the glucose residue of sucrose via an α-1,2 linkage. The compound is an unknown novel saccharide.

EXPERIMENT 13

Acute Toxicity Test

Acute toxicity test of the powdery products rich in glucosylsorbose, kojitriose, kojibiosylglucoside, and kojibiosylfructoside in Experiments 8–12 were tested in 7week-old dd-strain mice by administering orally. As a result, no mouse died even when administered with their maximum doses, i.e., 50 g/kg mouse by weight. The data indicates that these saccharides are extremely low in toxicity.

Example A explains the present kojibiose phosphorylase and saccharides containing glucosyl-transferred saccharides, DNA encoding the enzyme, and process for producing saccharide composition containing glucosyl-transferred saccharides prepared by using the enzyme; and Example B explains compositions which contain the saccharide compositions:

EXAMPLE A-1

Enzyme Solution

*Thermoanaerobium brockii*, ATCC 35047, was cultured by the method in Experiment 1 to obtain a seed culture, and one v/v % of the seed culture was inoculated into a fresh preparation of the same medium as used in Experiment 1, placed in an anaerobic fermenter according to the method in Experiment 1, and cultured at 65° C. for about 30 hours. The resulting culture was centrifuged to obtain cells which were then disrupted by ultrasonic and centrifuged, followed by measuring the kojibiose phosphorylase activity of the supernatant. The activity was 0.08 unit/ml culture. The supernatant of the disrupted cells was concentrated with an ultrafiltration membrane, and the concentrate was dialyzed to obtain an enzyme solution with an about 8 units/ml of kojibiose phosphorylase in a yield of about 70% to the total activity of the material culture.

EXAMPLE A-2

Preparation of DNA

According to the method in Experiment 1, a seed of *Thermoanaerobium brockii*, ATCC 35047, was inoculated into 11 L of a fresh preparation of the same nutrient culture medium in Experiment 1, and cultured at 60° C. for 24 hours. The proliferated cells were separated from the culture by centrifugation, suspended in an adequate amount of Tris-EDTA-saline buffer (hereinafter abbreviated as "TES buffer") (pH 8.0), admixed with 0.05 w/v % of lysozyme to the cell suspension, and incubated at 37° C. for 30 min. Thereafter, the enzyme-treated mixture was freezed at −80° C. for one hour, and admixed successively with TES buffer (pH 9.0) and a mixture solution of TES buffer-phenol heated to 60° C., followed by sufficiently stirring and cooling the mixture, centrifuging the resultant, and collecting the formed upper-layer. Twofold volumes of cool ethanol was added to the layer, and the formed sediment was collected, dissolved in an adequate amount of SSC buffer (pH 7.1), admixed with 7.5 μg ribonuclease and 125 μg protease, and incubated at 37° C. for one hour. To the resulting mixture was added a mixture solution of chloroform and isoamyl alcohol, followed by stirring and allowing to stand the mixture, and collecting the formed upper-layer. After adding cool ethanol to the layer, the formed sediment was collected, washed with 70 v/v % cool ethanol, and dried in vacuo to obtain a DNA. The DNA was dissolved in SSC buffer (pH 7.1) to give a concentration of about one mg/ml, and freezed at −80° C.

EXAMPLE A-3

Preparation of Transformant and Recombinant DNA

One ml of the DNA solution on Example A-2 was placed in a container, admixed with about 20 units of a restriction enzyme, Hind III, and incubated at 37° C. for 30 min to partially digest the DNA. The resulting mixture was subjected to sucrose density ultrafiltration to collect a DNA fragment of about 2,000–5,000 base pairs. In parallel, "BluescriptII SK(+)", a plasmid vector commercialized by Stratagene Cloning Systems, California, USA, was completely cleaved with a restriction enzyme, Hind III, and 0.3 μg of the cleaved vector and about 3 μg of the DNA fragment were ligated using "DNA LIGATION KIT", Takara Shuzo Co., Ltd., Otsu, Shiga, Japan, according to the procedure attached to the kit. Using the recombinant DNA thus obtained, 100 μg of "EPICURIAN COLI® XL1-BLUE", a microorganism of the species *Escherichia coli* commercialized by Stratagene Cloning Systems, California, USA, was transformed by conventional competent cell method to obtain a gene library.

The resulting transformants as a gene library were inoculated into agar plate (pH 7.0), prepared in a usual manner, containing 10 g/l trypton, 5 g/l yeast extract, 5 g/l sodium chloride, 75 mg/l sodium salt of ampicillin, and 50 mg/l 5-bromo-4-chloro-3-indolyl-β-galactoside, and cultured at 37° C. for 18 hours, followed by fixing about 4,000 white colonies, formed on the plate, onto "Hybond-N+", a nylon film commercialized by Amersham Corp., Div. Amersham International, Arlington, Heights, USA. Based on the amino acids 1–7 of SEQ ID NO: 7 revealed in Experiment 4, an oligonucleotide with a nucleotide sequence, represented by 5'-TTYGAYGARAAYAAYATGCC-3' (SEQ ID NO: 10), was chemically synthesized, and labelled with [γ-$^{32}$P]ATP and T4 polynucleotide kinase to obtain a synthesized DNA as a probe. Among the colonies fixed on the nylon film, a colony strongly hybridized with the probe was selected by applying conventional colony-hybridization method, and named "TKP1".

Figure 5:
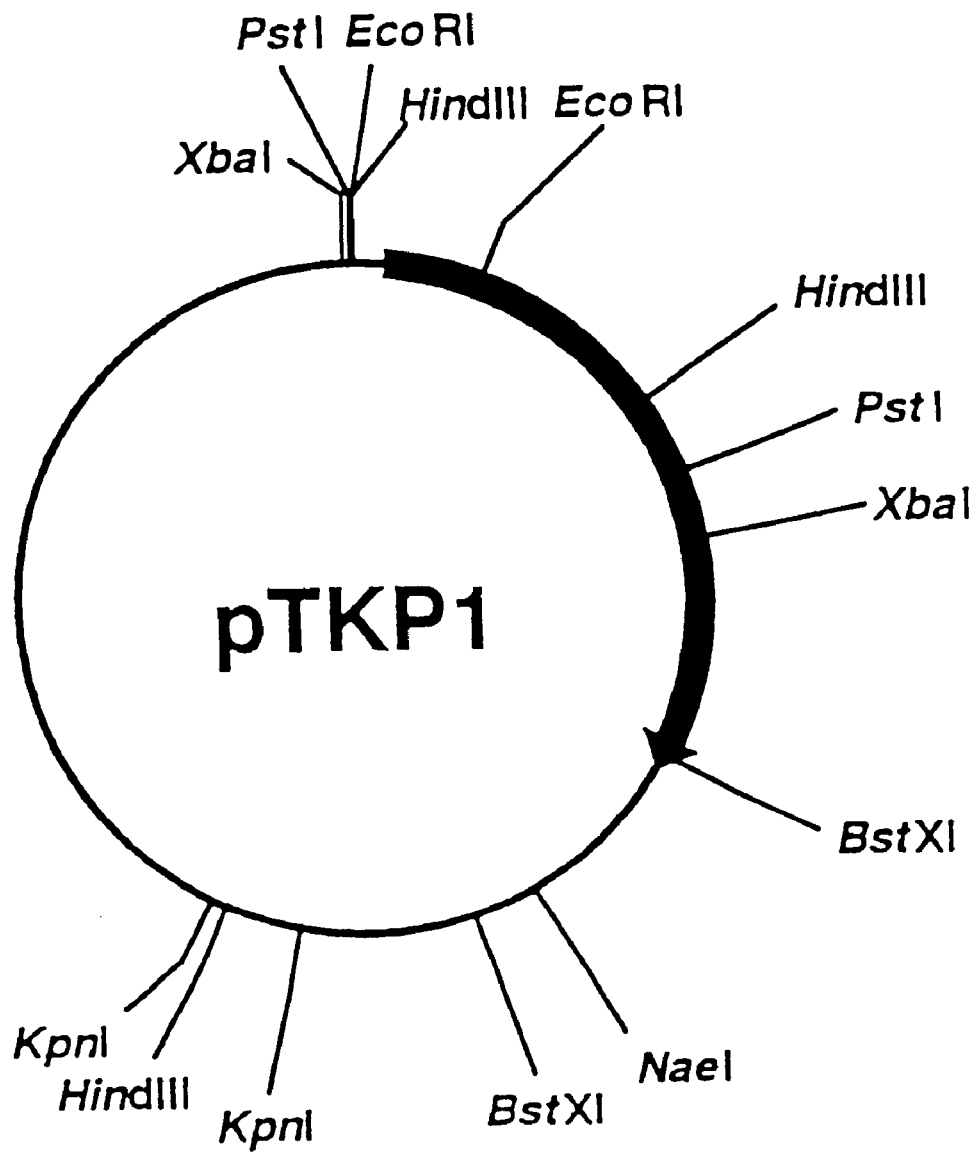
FIG. 5 is a restriction map of the recombinant DNA according to the present invention. In the figure, the arrow shows the DNA encoding the present kojibiose phosphorylase.

The transformant TKP1 was in a conventional manner inoculated into L-broth (pH 7.0) containing sodium salt of ampicillin, and incubated at 37° C. for 24 hours under rotary-shaking conditions. After completion of the culture, the culture was centrifuged to obtain cells which were then treated with conventional alkali-SDS method to extract a recombinant DNA. Conventional dideoxy analysis of the recombinant DNA revealed that it contained a DNA with the nucleotide sequence of SEQ ID NO: 9 consisting of 3,956 base pairs derived from *Thermoanaerobium brockii*, ATCC 35047. As shown in FIG. 5, the DNA was ligated to the downstream of a recognition site of a restriction enzyme, Hind III. An amino acid sequence deduced from the nucleotide sequence was as shown in SEQ ID NO: 9 in parallel. Comparing the amino acid sequence of SEQ ID NO: 9 with SEQ ID NOs: 1–3, which are the N-terminal amino acid sequences, and with SEQ ID NOs: 6–8, which are the internal amino acid sequences of the present kojibiose phosphorylase revealed in Experiment 4, the amino acid sequences of SEQ ID NOs: 1–3 were respectively coincided with the amino acids 1–5, 590–594, and 357–361 of SEQ ID NO: 9 as shown in parallel. The amino acid sequences of SEQ ID NOs: 6–8 were respectively coincided with the amino acids 1–10, 590–599, and 357–366 of SEQ ID NO: 9 as shown in parallel. These indicate that the present kojibiose phosphorylase has the amino acid sequence of SEQ ID NO: 4, and the enzyme of *Thermoanaerobium brockii*, ATCC 35047, is encoded by a DNA having the nucleotide sequence of SEQ ID NO: 5. The recombinant DNA, which was obtained by the above methods and revealed its nucleotide sequence, was named "pTKP1".

EXAMPLE A-4

Production of Kojibiose Phosphorylase by Transformant

One hundred milliliters of an aqueous solution, containing 16 g/l polypeptone, 10 g/l yeast extract, and 5 g/l sodium chloride, was placed in a 500-ml Erlenmeyer flask, autoclaved at 121° C. for 15 min, cooled, aseptically adjusted to pH 7.0, and aseptically admixed with 10 mg sodium salt of ampicillin into a liquid nutrient medium. The transformant TKP1 in Example A-3 was inoculated into the medium, and incubated at 37° C. for about 20 min under aeration-agitation conditions to obtain a seed culture. According to the preparation of the seed culture, 7 L of a fresh preparation of the same nutrient culture medium as used in the seed culture was placed in a 10-l fermenter, inoculated with 70 ml of the seed culture, and subjected to the incubation for about 20 hours under aeration-agitation conditions. The resulting culture was in a conventional manner centrifuged to collect cells which were then suspended in 10 mM phosphate buffer (pH 7.0), ultrasonicated for cell disruption, and centrifuged to remove impurities, followed by collecting a supernatant. The supernatant was dialyzed against 10 mM phosphate buffer, and assayed for kojibiose phosphorylase activity in the supernatant, revealing that about 500 units/l culture of the enzyme was produced.

As a first control, a seed of *Escherichia coli* XL1-Blue strain was inoculated into a nutrient culture medium similarly as in the culture of the above transformant except that the ampicillin was not added to the culture medium, and cultured. The proliferated cells were disrupted, followed by collecting and dialyzing the supernatant. As a second control, according to the method in Experiment 1, a seed of *Thermoanaerobium brockii*, ATCC 35047, was stationary cultured at 60° C. in a nutrient culture medium consisting of the same ingredients as used in the culture for the transformant except that the ampicillin was not used, and similarly as in the case of the transformant, the cells in the culture were disrupted, followed by collecting and dialyzing the supernatant. No enzyme activity of the present enzyme was detected in the dialyzed solution as the first control. The dialyzed solution as the second control had as enzyme activity of about 100 units/l culture which was lower than that of the transformant TKP1.

In accordance with the method in Experiment 2, the dialyzed solution in Example A-4 was purified on column chromatographies using "DEAE-TOYOPEARL® 650 GEL" and "ULTROGEL® AcA44 RESIN", and the purified enzyme was analyzed in accordance with the method in Experiment 3, revealing that it had a molecular weight of 83,000±5,000 daltons on SDS-PAGE, molecular weight of 500,000±30,000 daltons on gel filtration chromatography, isoelectric point of 4.4±0.5 on electrofocusing using polyacrylamide gel, optimum temperature of about 65° C., optimum pH of about 5.5, thermal stability of up to 65° C., and pH stability of about 5.5–10.0, all of which were substantially the same as those of the enzyme prepared in Experiments 1 and 2. These results indicate that the present kojibiose phosphorylase can be easily produced by recombinant DNA technology, and the enzyme yield can be significantly increased thereby.

EXAMPLE A-5

Enzyme Solution

The transformant TKP1 in Example A-3 was cultured by the method in Example A-4. The cells collected by centrifuging the culture were ultrasonicated, and the supernatant was assayed for kojibiose phosphorylase activity, resulting in an activity of about 0.5 unit/ml culture. The supernatant was concentrated with an ultrafiltration membrane and dialyzed to obtain an enzyme solution with about 10 units/ml of kojibiose phosphorylase in a yield of about 70% to the total enzyme activity of the material culture.

EXAMPLE A-6

Saccharide Solution Containing Kojibiose

To 25 mM of dipotassium hydrogenphosphate-citric acid buffer (pH 6.0) containing 5% maltose were added 5 units/g maltose of a commercially available bacterial maltose phosphorylase, and 40 units/g maltose of kojibiose phosphorylase obtained by the method in Example A-1, followed by incubation at 30° C. for 72 hours. The reaction mixture was heated at 100° C. for 30 min to inactivate the remaining enzyme, cooled, decolored with activated charcoals in a conventional manner, filtered, desalted and purified with ion exchange resins in H- and OH-form, and further concentrated to obtain a 75% syrupy saccharide solution containing kojibiose in a yield of about 95% to the material, d.s.b.

The product, which contains about 30% kojibiose, d.s.b., and kojibiosylglucose and has a satisfactory sweetness and an adequate viscosity and humectancy, can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-7

Kojibiose Rich Powder

A saccharide solution, as a material, containing about 30% kojibiose, d.s.b., obtained by the reaction and purification in Example A-6, was adjusted to give a concentration of about 20%, d.s.b., which was then mixed with 5 units/g dry solid of glucoamylase and incubated at pH 4.5 and 40° C. for 16 hours to decompose the remaining maltose. The reaction mixture was heated at 100° C. for 30 min to suspend the enzymatic reaction, then concentrated into an about 40% solution. To increase the kojibiose content, the concentrated solution was fractionated by providing four jacketed-stainless steel columns, 3 cm in diameter and one m in length each, packed with a water suspension of "XT-1016", an alkali metal strong-acid cation exchange resin, Na-form, polymerization degree of 4%, commercialized by Tokyo Organic Chemical Industries, Ltd., Tokyo, Japan, which were cascaded in series to give a total gel-bed depth of about 4 m, feeding 5 v/v % of the solution to the resin, fractionating the solution by feeding water heated to 40° C. to the columns at SV 0.15, and collecting the kojibiose rich fractions. The fractions were pooled, concentrated, dried in vacuo, and pulverized to obtain a kojibiose rich powder in a yield of about 20% to the material, d.s.b.

The product contains about 90% kojibiose, d.s.b., and has a satisfactorily tastable sweetness and adequate humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-8

Saccharide Solution Containing Glucosylsorbose

An aqueous solution containing β-D-glucose-1-phosphoric acid and L-sorbose in a respective concentration of 5%, adjusted to give a pH of 5.5, mixed with 10 units/g β-D-glucose-1-phosphoric acid of a kojibiose phosphorylase obtained by the method in Example A-1, and enzymatically reacted at 60° C. for 72 hours. The reaction mixture was heated at 90° C. for 30 min to inactivate the remaining enzyme, cooled, decolored with activated charcoals in a conventional manner, filtered, desalted and purified with ion exchange resins in H- and OH-form, and further concentrated to obtain an about 75% syrupy saccharide solution containing glucosylsorbose in a yield of about 95% to the material, d.s.b.

The product contains about 30% kojibiose, d.s.b., and has a satisfactorily tastable sweetness and adequate, viscosity and humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-9

Saccharide Solution Rich in Glucosylsorbose

As aqueous solution, containing 5% β-D-glucose-1-phosphoric acid and 10% L-sorbose, was adjusted to give a pH of 6.0, mixed with 30 units/g β-D-glucose-1-phosphoric acid of kojibiose phosphorylase obtained by the method in Example A-1, and enzymatically reacted at 60°0 C. for 72 hours. The reaction mixture was cooled, mixed with 5% of a commercially available bakers' yeast by wet weight, and enzymatically reacted at 27° C. for 6 hours while controlling the pH at ones in the range of 5–6 by the addition of 1-N sodium hydroxide solution. The reaction mixture heated at 90° C. for 30 min to suspend the enzymatic reaction, cooled, decolored, and purified with ion exchange resins in H- and OH-form in a conventional manner, and further concentrated to obtain an about 75% syrupy saccharide solution containing glucosylsorbose in a yield of about 65% to the material, d.s.b.

The product contains about 40% glucosylsorbose, d.s.b., and has a satisfactorily tastable sweetness and adequate viscosity and humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-10

Glucosylsorbose Rich Powder

A saccharide solution, as a material, containing about 40% glucosylsorbose, d.s.b., obtained by the reaction and purification of Example A-9, was adjusted to give a concentration of about 45%, d.s.b. To increase the content of glucosylsorbose, the resulting solution was fractionated by providing four jacketed-stainless steel columns 3 cm in diameter and one m in length each, which were packed with a water suspension of "XT-1016", an alkali metal strong-acid cation exchange resin, Na-form, polymerization degree of 4%, commercialized by Tokyo Organic Chemical Industries, Ltd., Tokyo, Japan, and cascaded in series to give a total gel-bed depth of about 4 m, feeding 5 v/v % of the solution to the resin, fractionating the solution by feeding water heated to 40° C. to the columns at SV 0.15, and collecting the resulting glucosylsorbose rich fractions. The fractions were pooled, concentrated, dried in vacuo, and pulverized to obtain a glucosylsorbose rich powder in a yield of about 25% to the material, d.s.b.

The product contains about 90% glucosylsorbose, d.s.b., and has a satisfactorily tastable sweetness and adequate humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-11

Saccharide solution containing kojibiosylfructoside

An aqueous solution containing 10% kojibiose and 10% sucrose was prepared, admixed with 40 units/g kojibiose of kojibiose phosphorylase obtained by the method in Example A-1, and enzymatically reacted in the presence of 5 mM sodium dihydrogenphosphate at pH 5.0 and 60° C. for 72 hours. The reaction mixture was heated at 90° C. for 30 min. to inactivate the remaining enzyme, cooled, decolored with activated charcoal in a conventional manner, filtered, desalted and purified with ion exchange resins in H- and OH-form, and further concentrated to obtain an about 75% syrupy saccharide solution in a yield of about 95% to the material, d.s.b.

The product contains about 55% kojibiosylfructoside, d.s.b., and has a satisfactorily tastable sweetness and adequate viscosity and humectancy, and it can be arbitrarily used in food products, cosmetics, pharmaceuticals, and shaped bodies.

EXAMPLE A-12

Kojibiosylfructoside rich powder

A saccharide solution as a material containing about 55% kojibiosylfructoside, d.s.b., obtained by the reaction and purification in Example A-11, was adjusted to give a concentration of about 45%, d.s.b. To increase the content of kojibiosyl-fructoside, the resulting solution was column chromatographed according to the method in Example A-10 except for using "DOWEX 50WX4 (Ca-form)", an alkaline-earth metal strong-acid cation exchange resin commercialized by the Dow Chemical Co., Midland, Mich., USA, to collect kojibiosylfructoside rich fractions. The fractions were pooled, purified, concentrated, dried in vacuo, and pulverized to obtain a kojibiosylfructoside rich powder in a yield of about 40%, d.s.b.

The product contains about 95% kojibiosylfructoside, d.s.b., and has a satisfactorily tastable sweetness and adequate humectancy, and it can be arbitrarily used in food products, cosmetics, pharmaceuticals, and shaped bodies.

EXAMPLE A-13

Saccharide solution containing kojibiosylglucose

An aqueous solution, containing about 10% β-D-glucose-1-phosphoric acid and 20% maltose, was adjusted to give a pH of 5.0, mixed with 40 units/g maltose of a kojibiose phosphorylase obtained by the method in Example A-1, and enzymatically reacted at 60° C. for 72 hours. The reaction mixture was heated at 90° C. for 30 min to inactivate the remaining enzyme, cooled, decolored with activated charcoals in a conventional manner, filtered, desalted and purified with ion exchange resins in H- and OH-form, and further concentrated to obtain an about 75% syrupy saccharide solution containing kojibiosylglucose in a yield of about 95% to the material, d.s.b.

The product contains about 45% kojibiosylglucose, d.s.b., and has a satisfactorily tastable sweetness and adequate viscosity and humectancy, and it can be arbitrarily used in food products, cosmetics, pharmaceuticals, and shaped bodies.

EXAMPLE A-14

Saccharide solution rich in kojibiosylglucoside

An aqueous solution, containing about 5% β-D-glucose-1-phosphoric acid and 10% trehalose, was adjusted to give a pH of 5.0, mixed with 20 units/g β-D-glucose-1-phosphoric acid of a kojibiose phosphorylase obtained by the method in Example A-1, and enzymatically reacted at 60° C. for 72 hours. The reaction mixture was heated at 100° C. while keeping the pH to alkaline pHs of over 10, cooled, decolored with activated charcoals in a conventional manner, filtered, desalted and purified with ion exchange resins in H- and OH-form, and further concentrated to obtain an about 75% syrupy saccharide solution rich in kojibiosylglucoside in a yield of about 60% to the material, d.s.b.

The product contains about 95% kojibiosylglucose, d.s.b., and has a satisfactorily tastable sweetness and adequate viscosity and humectancy, and it can be arbitrarily used in food products, cosmetics, pharmaceuticals, and shaped bodies.

EXAMPLE A-15

Saccharide solution containing kojibiose

To 25 mM dipotassium hydrogenphosphate-citrate buffer (pH 6.0) containing 5% maltose were added 5 units/g maltose of a commercialized available bacterial maltose-phosphorylase and 40 units/g maltose of a kojibiose phosphorylase obtained by the method in Example A-5, followed by the incubation at 37° C. for 72 hours, The reaction mixture was heated at 100° C. for 30 min to inactivate the remaining enzyme, cooled, and in a conventional manner decolored with activated charcoals, filtered, desalted and purified on ion exchangers in H- and OH-form., and further concentrated to obtain an about 75% syrupy saccharide solution containing kojibiose in a yield of about 95% to the material, d.s.b.

Since the product contains about 30% kojibiose, d.s.b., and kojibiosylglucose, and has a satisfactorily tastable sweetness, adequate viscosity and humectancy, it can be arbitrarily used in food products, cosmetics, pharmaceuticals, and shaped bodies as a sweetener, quality-improving agent, stabilizer, growth-promoting agent for bifid bacteria, and mineral-absorption-promoting agent.

EXAMPLE A-16

Saccharide solution rich in kojibiosylglucoside

An aqueous solution, containing 5% β-D-glucose-1-phosphoric acid and 10% trehalose, was adjusted to pH 5.0, admixed with 20 units/g β-D-glucose-1-phosphoric acid of a kojibiose phosphorylase obtained by the method in Example A-5, and subjected to an enzymatic reaction at 60° C. for 72 hours. The reaction mixture was heated at 100° C. while controlling the pH over 10 by the addition of sodium hydroxide, cooled, and in a conventional manner decolored with activated charcoals, filtered, desalted and purified on ion exchangers in H- and OH-form., and further concentrated to obtain an about 75% syrupy saccharide solution containing kojibiosylglucoside in a yield of about 60% to the material, d.s.b.

Since the product contains about 95% kojibiosylglucoside, d.s.b., and has a satisfactorily tastable sweetness, adequate viscosity and humectancy, it can be arbitrarily used in food products, cosmetics, pharmaceuticals, and shaped bodies.

EXAMPLE B-1

Sweetener

To one part by weight of a glucosylsorbose rich powder, obtained by the method in Example A-10, was added 0.05 part by weight of "αG Sweet", an α-glycosyl stevioside commercialized by Toyo Sugar Refining Co., Ltd. Tokyo, Japan, and the mixture was mixed to homogeneity into a powdery sweetener. The product is a high-quality sweetener with an about twofold-higher sweetening power of sucrose and a half calorific value of sucrose with respect to the sweetening powder. Therefore, the product can be satisfactorily used as a low-calorie sweetener to sweeten low-calorie food products for persons, who are restricted to take less calories, such as fat persons and diabetics. Since the product less produces insoluble glucans and acids by dental caries-inducing microorganisms, it can be suitably used to sweeten dental-caries inhibitory food products.

EXAMPLE B-2

Hard candy

Thirty parts by weight of a saccharide solution containing glucosylsorbose, obtained by the method in Example A-8, was added to and dissolved by mixing in 80 parts by weight of hydrogenated malt syrup with a moisture content of 25%, and the resulting solution was concentrated up to give a moisture content of below 2%, kneaded with one part by weight of citric acid and adequate amounts of a lemon flavor and coloring agent, followed by kneading and shaping the mixture into a hard candy. The product has a high-quality sweetness, lower humectancy, and satisfactory biting property without causing melting.

EXAMPLE B-3

Chewing gum

Four parts by weight of a powder rich in kojibiosylfructoside, obtained by the method in Example A-12, was admixed with 3 parts by weight of glucose and 2 parts by weight of a gum base which had been melted by heating until softened, and further mixed with an adequate amount of a mint flavor followed shaping the mixture by kneading with a roll into a chewing gum. The product has a satisfactory texture and flavor.

EXAMPLE B-4

Chocolate

Fifteen parts by weight of a powder rich in kojibiose, obtained by the method in Example A-7, was mixed with 40 parts by weight of cacao paste, 10 parts by weight of cacao butter, 10 parts by weight of sucrose, and 15 parts by weight of skim milk, and the mixture was passed through a refiner to lower the granular size. Thereafter, the resulting mixture was placed in a conche, mixed with 0.5 part by weight of lecithin, and kneaded up at 50° C. for two days and nights. The kneaded mixture was poured into a molding machine, shaped, and solidified into a chocolate. The product free of fat- and sugar-blooms has a satisfactory taste, flavor, and meltability on your tongue.

EXAMPLE B-5

Custard cream

To 400 parts by weight of a powder rich in glucosyl-sorbose, obtained by the method in Example A-10, were added 500 parts by weight of corn starch, 500 parts by weight of maltose, and 5 parts by weight of salt, and the mixture was sufficiently mixed by passing through a sieve, mixed with 1,400 parts by weight of fresh eggs, stirred, gradually admixed with 5,000 parts by weight of a boiling milk, and heated over a slow fire while stirring. The heating was suspended when the corn starch completely gelatinized to show semitransparency, then cooled, mixed with a small amount of a vanilla flavor to obtain a custard cream. The product has a smooth surface and satisfactory taste free of strong sweetness.

EXAMPLE B-6

Uiro (starch paste)

To 90 parts by weight of a saccharide solution containing kojibiosylfructoside, obtained by the method in Example A-11, were added 90 parts by weight of rice powder, 20 parts by weight of corn starch, 20 parts by weight of sugar, one part by weight of matcha (a green tee) powder, and an adequate amount of water, and the mixture was kneaded, placed in a container, and steamed for 60 min into a matcha uiro. The product has a satisfactory gloss, biting property, flavor, and taste. The retrogradation of starch is well prevented, resulting in a relatively-long shelf life.

EXAMPLE B-7

Bettara-zuke (fresh radish pickles)

A premix for bettara-zuke was prepared by mixing to homogeneity one part by weight of a saccharide solution containing kojibiosylglucose, obtained by the method in Example A-13, with 3 parts by weight of maltose, 0.05 part by weight of a licorice preparation, 0.008 part by weight of malic acid, 0.07 part by weight of sodium glutamate, 0.03 part by weight of potassium sorbate, and 0.2 part by weight of pullulan. Thirty kilograms of radish was first pickled with salt in a conventional manner, then pickled with sugar, and soaked in a seasoning solution, prepared with 4 kg of the premix, into the desired product. The product has a satisfactory color, gloss, and fragrance, as well as an adequate sweetness, and satisfactory biting property.

EXAMPLE B-8

Beverage with lactic acid bacteria

One hundred and thirty parts by weight of a saccharide solution containing kojibiose, obtained by the method in Example A-6, 175 parts by weight of skim milk, and 50 parts by weight of "NYUKAOLIGO®", a high lactosucrose content powder commercialized by Hayashibara Shoji, Inc., Okayama, Japan, were dissolved in 1,150 parts by weight of water, and the solution was sterilized at 65° C. for 30 min, cooled to 40° C., and in a conventional manner inoculated with 30 parts by weight of lactic acid bacteria as a starter, followed by the incubation at 37° C. for 8 hours to obtain the desired product. The product is a beverage containing lactic acid bacteria and having a satisfactory flavor and taste. The product contains oligosaccharides which stabilize the bacteria and promote the growth.

EXAMPLE B-9

Synthetic liquor

A raw liquor with about 20 v/v % alcohol was obtained by mixing 6,518 parts by weight of 30 v/v % aqueous alcohol solution with a temperature of 15° C., 600 parts by weight of 70% aqueous glucose solution, 50 parts by weight of a saccharide solution containing kojibiose obtained by the method in Example A-6, 11.1 parts by weight of succinic acid, 3.66 parts by weight of 75% aqueous lactic acid solution, 2.3 parts by weight of sodium glutamate, 1.2 parts by weight of glycine, 1.2 parts by weight of alanine, 2.22 parts by weight of sodium succinate, 1.6 parts by weight of salt, 1.4 parts by weight of natural salt, and 2,500 parts by weight of water. The raw liquour was diluted with water into a liquor with 15–16 v/v % alcohol. The product has a mild sweetness and high quality flavor, taste, and deliciousness.

EXAMPLE B-10

Milky lotion

To 3.5 parts by weight of a saccharide solution rich in glucosylsorbose, obtained by the method in Example A-9, were added 0.5 part by weight of polyoxyethylene behenyl ether, one part by weight of polyoxyethylene sorbitol tetraoleate, one part by weight of oil-soluble glycerol monostearate, 0.5 part by weight of behenyl alcohol, one part by weight of avocado oil, one part by weight of α-glycosylrutin, and adequate amounts of vitamin E and an antiseptic, and the mixture was dissolved by heating. The resulting solution was mixed with 5 parts by weight of 1,3-butylene glycol, 0.1 part by weight of carboxyvinyl polymer, and 85.3 parts by weight of refined water, and the mixture was emulsified by a homogenizer into a milky lotion.

The product with a satisfactory humectancy can be arbitrarily used as a sunscreen, and skin-whitening agent.

EXAMPLE B-11

Skin cream

To 4 parts by weight of a powder rich in kojibiosylfructoside, obtained by the method in Experiment 12, were added 2 parts by weight of polyoxyethylene glycol monostearate, 5 parts by weight of self-emulsifying glycerine monostearate, 2 parts by weight of α-glycosyl rutin, one part by weight of liquid paraffin, 10 parts by weight of glycerol trioctanate, and an appropriate amount of an antiseptic, and the mixture was dissolved by heating in a conventional manner, mixed with 5 parts by weight of 1,3-butylene glycol, and 66 parts by weight of refined water, emulsified with a homogenizer, and mixed with an appropriate amount of a flavor into a skin cream. The product with a well-spreadability can be arbitrarily used as a sunscreen, skin-refining agent, and skin-whitening agent.

EXAMPLE B-12

Toothpaste

An adequate amount of calcium monohydrogenphosphate, 1.5 parts by weight of sodium lauryl sulfate, 25 parts by weight of glycerine, 0.5 part by weight of polyoxyethylene sorbitan laurate, 0.02 part by weight of saccharin, 0.05 part by weight of an antiseptic, and 13 parts by weight of water were mixed with 15 parts by weight of a saccharide solution rich in kojibiosylglucoside, obtained by the method in Example A-14, into a toothpaste.

The product, having a superior gloss and detergency, can be suitably used as a dentifrice.

EXAMPLE B-13

Nutrition for intubation feeding

A composition, consisting of 80 parts by weight of a powder rich in kojibiose obtained by the method in Example A-7, 190 parts by weight of dried egg yolk, 209 parts by weight of skim milk, 4.4 parts by weight of sodium chloride, 1.85 parts by weight of potassium chloride, 4 parts by weight of magnesium sulfate, 0.01 part by weight of thiamine, and 0.1 part by weight of sodium ascorbate, 0.6 part by weight of vitamin E acetate, and 0.04 part by weight of nicotine amide, was prepared. Twenty-five grams aliquots of the composition were injected into small laminated aluminum bags which were then heat-sealed to obtain the desired product.

One bag of the product is dissolved in about 150–300 ml water into a supplemental nutrition feeding to be administered to the nasal cavity, throat, and stomach.

EXAMPLE B-14

Tablet

Fifty parts by weight of aspirin, 10 parts by weight of maltose, 4 parts by weight of corn starch were added to 4 parts by weight of a powder rich in glucosylsorbose obtained by the method in Experiment 8, and the mixture was mixed to homogeneity, and tabletted with a 20R-punch with a diameter of 12 mm into tablets, 680 mg weight, 5.25 mm thickness, 8 kg±1 kg hardness each. The product with an adequate sweetness is an easily swallowable tablet.

EXAMPLE B-15

Strawberry jam

One hundred and fifty parts by weight of fresh strawberries, 60 parts by weight of sucrose, 20 parts by weight of maltose, 40 parts by weight of a saccharide solution containing kojibiose obtained by the method in Example A-15, 5 parts by weight of pectin, and one part by weight of citric acid. The mixture was boiled up in a pan and bottled into the desired product. The product has a satisfactory taste, flavor, and color.

EXAMPLE B-16

Sweetened condensed milk

In 100 parts by weight of fresh milk were dissolved one part by weight of sucrose and 3 parts by weight of a saccharide solution rich in kojibiosylglucoside obtained by the method in Example A-16, and the solution was sterilized by heating on a plate heater, condensed to give a concentration of about 70%, and aseptically canned into the desired product. The product has a mild sweetness, flavor, and taste, and it can be arbitrarily used as a seasoning for food for infants, fruits, coffees, cocoas, and teas.

As evident from the above, the present invention was made based on a finding of an unknown kojibiose-forming phosphorylase, i.e., kojibiose phosphorylase. The kojibiose phosphorylase according to the present invention has a relatively-high optimum temperature and thermal stability, and relatively-wide range pH-stability in which the optimum pH lies. The kojibiose phosphorylase can be produced by microorganisms capable of producing the enzyme in a satisfactorily-high yield. Thus, when the present kojibiose phosphorylase is allowed to contact with β-D-glucose-1-phosphoric acid as as saccharide donor in the presence of other saccharides, compounds including kojibiose which are conventionally known but scarcely obtainable, glucosyl-transferred saccharides such as novel glucosylsorbose, and saccharide compositions containing the glucosyl-transferred saccharides can be produced in an industrial-scale and relatively-low cost.

The glucosyl-transferred saccharides and saccharide compositions containing the same can be used as sweeteners with a relatively-high quality sweetness, taste-improving agents, quality-improving agents, body-imparting agents, viscosity-controlling agents, moisture-controlling agents, gloss-imparting agents, and supplemental nutrition agents in food products, cosmetics, pharmaceuticals, and shaped bodies. Because of these outstanding characteristics of the present invention, it greatly contributes to food, cosmetic, and pharmaceutical fields, and to agriculture, fishery, breeding, and chemical industries.

While there has been described what is at present considered to be the preferred embodiments of the invention, it will be understood the various modifications may be made therein, and it is intended to cover in the appended claims all such modifications as fall within the true spirits and scope of the invention.

What is claimed is:

1. An isolated or purified DNA consisting of an open reading frame encoding kojibiose phosphorylase, wherein the encoded kojibiose phosphorylase has the following characteristics:

(1) catalyzes the phosphorolysis of kojibiose to form D-glucose and β-D-glucose-1-phosphoric acid and/or its salt;

(2) has an isoelectric point of about pI 4.4±0.5 on electrophoresis using ampholyte;

(3) has a molecular weight of about 83,000±5,000 Daltons on SDS-PAGE; and (4) is obtainable from microorganisms of the genus Thermoanaerobium.

2. A DNA construct into which the DNA of claim 1 is inserted.

3. A self-replicable vector comprising the DNA construct of claim 2.

4. A host cell comprising the self-replicable vector of claim 3.

5. The DNA of claim 1, wherein the encoded kojibiose phosphorylase comprises the sequence set forth in SEQ ID NO:4.

6. A DNA construct into which the DNA of claim 5 is inserted.

7. A self-replicable vector comprising the DNA constructed of claim 6.

8. A host cell comprising the self-replicable vector of claim 7.

9. The DNA of claim 1, wherein the open reading frame comprises the sequence set forth in SEQ ID NO:5.

10. A DNA construct into which the DNA of claim 9 is inserted.

11. A self-replicable vector comprising the DNA construct of claim 10.

12. A host cell comprising the self-replicable vector of claim 11.

13. An isolated or purified DNA consisting of an open reading frame encoding a polypeptide having kojibiose phosphorylase activity, wherein the encoded polypeptide is an active fragment of the kojibiose phosphorylase encoded by the DNA of claim 1.

14. A DNA construct into which the DNA of claim 13 is inserted.

15. A self-replicable vector comprising the DNA construct of claim 14.

16. A host cell comprising the self-replicable vector of claim 15.

* * * * *

SEQUENCE LISTING

```
(1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH:5 amino acids
        (B) TYPE:amino acid
        (D) TOPOLOGY:linear (ii) MOLECULE TYPE:peptide (v) FRAGMENT TYPE:N-terminal fragment (xi) SEQUENCE DESCRIPTION:SEQ ID NO:1:

Met Val Lys His Met
1               5

(2) INFORMATION FOR SEQ ID NO:2:

(i) SEQUENCE CHARACTERISTICS:
        (A) LENGTH:5 amino acids
        (B) TYPE:amino acid
        (D) TOPOLOGY:linear (ii) MOLECULE TYPE:peptide (v) FRAGMENT TYPE:internal fragment
```

```
        (xi) SEQUENCE DESCRIPTION:SEQ ID NO:2:

Phe Asp Glu Asn Asn
1               5

(2) INFORMATION FOR SEQ ID NO:3:

(i) SEQUENCE CHARACTERISTICS:
            (A) LENGTH:5 amino acids
            (B) TYPE:amino acid
            (D) TOPOLOGY:linear (ii) MOLECULE TYPE:peptide (v) FRAGMENT TYPE:internal fragment (xi) SEQUENCE DESCRIPTION:SEQ ID NO:3:

Gly His Val Phe Trp
1               5

(2) INFORMATION FOR SEQ ID NO:4:

(i) SEQUENCE CHARACTERISTICS:
            (A) LENGTH:775 amino acids
            (B) TYPE:amino acid
            (D) TOPOLOGY:linear (ii) MOLECULE TYPE:peptide (xi) SEQUENCE DESCRIPTION:SEQ ID NO:4:

Met Val Lys His Met Phe Leu Glu Asp Val Asn Asn Leu Ile Ser Asp
1               5                   10                  15

Asp Lys Trp Leu Ile Phe Gln Asn Glu Tyr Asn Thr Glu Val Asn Pro
                20                  25                  30

Arg Tyr Glu Thr Leu Phe Thr Leu Thr Asn Gly Tyr Met Gly Val Arg
            35                  40                  45

Gly Thr Phe Glu Glu Gly Ser Glu Gly Glu Arg Ser Gly Asn Phe Ile
        50                  55                  60

Ala Gly Ile Phe Asp Lys Ser Asp Ala Gln Val Arg Glu Ile Val Asn
65                  70                  75                  80

Ala Gln Asn Trp Leu Arg Ile Lys Leu Tyr Val Glu Gly Glu Glu Leu
                85                  90                  95

Ser Leu Asp Lys Cys Gln Leu Ile Glu Phe Lys Arg Ile Leu Asp Met
                100                 105                 110

Lys Lys Gly Ile Leu Phe Arg Ser Met Leu Ile Lys Asp Ser Lys Asp
                115                 120                 125

Arg Ile Thr Arg Ile Glu Gly Tyr Arg Phe Ile Ser Arg Ser Asp Leu
                130                 135                 140

His Arg Ser Ala Ile Lys Leu Phe Val Thr Pro Val Asn Tyr Ser Gly
145                 150                 155                 160

Val Val Gly Ile Glu Ser Ile Ile Asp Gly Thr Val Leu Asn Ser Ala
                165                 170                 175
```

-continued

```
Asp Ser Pro Lys His Arg Val Lys His Leu Lys Val Ala Asp Asn Ser
            180                 185                 190

Ser Leu Asn Lys Ser Gly Val Tyr Leu Glu Thr Ala Thr Ile Asp Asp
            195                 200                 205

Asp Ile Arg Ile Ala Thr Gly Ser Ala Val Arg Leu Tyr His Tyr Glu
210                 215                 220

Asp Lys Glu Lys Asn Asn Ile Ala Lys Phe Lys Arg Phe Leu Pro Leu
225                 230                 235                 240

Gly Glu Met Ser Ile Glu Tyr Phe Glu Phe Asp Gly Thr Glu Asn Lys
                245                 250                 255

Thr Val Val Ile Asp Lys Phe Ile Ile Thr Tyr Thr Ser Arg Asp Val
            260                 265                 270

Lys Lys Gly Leu Leu Lys Ser Thr Val Glu Lys Glu Leu Phe Ala Phe
            275                 280                 285

Ala Gly Glu Gly Ile Asp Lys Glu Leu Gln Arg His Ile Glu Val Tyr
290                 295                 300

Glu Glu Leu Trp Ser Val Ala Asp Ile Asn Ile Glu Gly Asp Glu Glu
305                 310                 315                 320

Ala Asp Lys Ala Leu Arg Phe Asn Ile Phe His Leu Met Ser Ser Val
                325                 330                 335

Asn Glu Asn Asp Pro Met Val Ser Ile Ala Ala Lys Ala Leu His Gly
            340                 345                 350

Glu Gly Tyr Lys Gly His Val Phe Trp Asp Thr Glu Ile Phe Met Leu
            355                 360                 365

Pro Phe Phe Ile Tyr Val His Pro Lys Ala Ala Lys Thr Leu Leu Met
370                 375                 380

Tyr Arg Tyr Asn Met Leu Asp Ala Ala Arg Lys Asn Ala Ala Leu Asn
385                 390                 395                 400

Gly Tyr Lys Gly Ala Gln Tyr Pro Trp Glu Ser Ala Asp Thr Gly Glu
                405                 410                 415

Glu Glu Thr Pro Lys Trp Gly Phe Asp Tyr Met Gly Asn Pro Val Arg
            420                 425                 430

Ile Trp Thr Gly Asp Leu Glu His His Ile Thr Ala Asp Ile Ala Phe
            435                 440                 445

Ala Val Trp Glu Tyr Phe Arg Ala Thr Glu Asp Ile Glu Phe Met Leu
450                 455                 460

Asn Tyr Gly Ala Glu Val Ile Phe Glu Thr Ala Arg Phe Trp Val Ser
465                 470                 475                 480

Arg Cys Glu Tyr Val Lys Glu Leu Asp Arg Tyr Glu Ile Asn Asn Val
                485                 490                 495
```

-continued

```
Ile Gly Pro Asp Glu Phe His Glu His Val Asp Asn Asn Ala Tyr Thr
            500                 505                 510

Asp Tyr Leu Ala Lys Trp Asn Ile Lys Lys Gly Leu Glu Leu Ile Asn
            515                 520                 525

Met Leu Lys Glu Lys Tyr Pro Glu His Tyr His Ala Ile Ser Asn Lys
        530                 535                 540

Lys Cys Leu Thr Asn Glu Glu Met Glu Lys Trp Lys Glu Val Glu Glu
545                 550                 555                 560

Lys Ile Tyr Ile Pro Tyr Asp Asp Lys Lys Leu Ile Glu Gln Phe
                565                 570                 575

Glu Gly Tyr Phe Asp Lys Asp Tyr Val Ile Asp Lys Phe Asp Glu
                580                 585                 590

Asn Asn Met Pro Ile Trp Pro Glu Gly Val Asp Ile Thr Lys Leu Gly
        595                 600                 605

Asp Thr Gln Leu Ile Lys Gln Ala Asp Val Val Met Leu Met Leu Leu
        610                 615                 620

Leu Gly Glu Glu Phe Asp Glu Thr Lys Arg Ile Asn Tyr Glu Tyr
625                 630                 635                 640

Tyr Glu Lys Arg Thr Met His Lys Ser Ser Leu Gly Pro Ser Met Tyr
                645                 650                 655

Ala Ile Met Gly Leu Lys Val Gly Asp His Lys Asn Ala Tyr Gln Ser
                660                 665                 670

Phe Met Arg Ser Ala Asn Val Asp Leu Val Asp Asn Gln Gly Asn Thr
        675                 680                 685

Lys Glu Gly Leu His Ala Ala Ser Ala Gly Gly Thr Trp Gln Val Val
        690                 695                 700

Val Phe Gly Phe Gly Gly Met Glu Ile Asp Lys Glu Gly Ala Leu Asn
705                 710                 715                 720

Ile Asn Ser Trp Leu Pro Glu Lys Trp Asp Lys Leu Ser Tyr Lys Val
                725                 730                 735

Phe Trp Lys Gly Asn Leu Ile Glu Val Ile Val Thr Lys Gln Glu Val
                740                 745                 750

Thr Val Lys Lys Leu Lys Gly Lys Gly Asn Ile Lys Val Lys Val Lys
        755                 760                 765

Gly Lys Glu Leu Thr Ile Glu
        770                 775
```

(2) INFORMATION FOR SEQ ID NO:5:

(i) SEQUENCE CHARACTERISTICS:
        (A) LENGTH:2325 base pairs
        (B) TYPE:nucleic acid
        (C) STRANDEDNESS:double (D) TOPOLOGY:linear (xi) SEQUENCE DESCRIPTION:SEQ ID NO:5:

| | | | | | |
|---|---|---|---|---|---|
| GTGGTAAAGC | ACATGTTTTT | AGAGGATGTA | AACAATTTAA | TAAGTGATGA | CAAATGGCTT | 60 |
| ATTTTCCAAA | ATGAGTATAA | TACAGAGGTA | AATCCTCGAT | ATGAGACCCT | TTTTACACTT | 120 |
| ACAAATGGTT | ACATGGGCGT | AAGAGGTACT | TTTGAGGAAG | GAAGCGAGGG | AGAAAGGTCG | 180 |
| GGAAATTTTA | TTGCAGGAAT | TTTTGACAAG | TCAGATGCGC | AGGTTAGAGA | AATAGTAAAT | 240 |
| GCTCAAAATT | GGTTGAGAAT | AAAGTTGTAT | GTTGAAGGTG | AAGAATTAAG | TTTGGATAAA | 300 |
| TGCCAGTTGA | TAGAATTTAA | AAGAATTCTT | GATATGAAAA | AAGGTATTCT | ATTTAGGAGT | 360 |
| ATGTTGATAA | AAGACAGCAA | AGATAGAATT | ACTCGAATTG | AGGGATACAG | GTTTATAAGC | 420 |
| CGTAGCGACC | TTCATCGTTC | TGCAATTAAG | CTATTTGTAA | CACCTGTAAA | TTACAGTGGT | 480 |
| GTTGTAGGTA | TAGAGAGCAT | TATTGATGGG | ACTGTTTTAA | ATTCAGCAGA | TAGCCCAAAG | 540 |
| CATAGGGTAA | AGCATTTGAA | AGTGGCTGAC | AATAGCAGTT | TAAATAAAAG | CGGAGTTTAT | 600 |
| CTTGAAACAG | CAACTATTGA | CGATGATATT | CGCATTGCAA | CAGGTAGTGC | AGTGAGGTTA | 660 |
| TATCATTATG | AGGATAAAGA | GAAAAATAAC | ATAGCTAAAT | TTAAGAGATT | TTTGCCTTTA | 720 |
| GGTGAAATGA | GTATTGAATA | CTTTGAGTTT | GATGGCACAG | AGAACAAAAC | AGTAGTAATT | 780 |
| GACAAATTTA | TTATAACCTA | TACCTCAAGA | GACGTAAAAA | AAGGCCTATT | AAAGAGTACG | 840 |
| GTGGAAAAAG | AACTCTTTGC | TTTTGCTGGA | GAAGGTATTG | ACAAAGAGTT | GCAGAGACAT | 900 |
| ATTGAGGTAT | ATGAAGAACT | ATGGTCTGTT | GCAGATATAA | ATATTGAAGG | GGATGAAGAA | 960 |
| GCAGATAAAG | CTTTGAGGTT | TAATATTTTT | CATCTCATGA | GTTCTGTCAA | TGAAAATGAC | 1020 |
| CCCATGGTAA | GTATCGCTGC | AAAGGCCCTT | CATGGTGAGG | GATACAAAGG | CCATGTCTTT | 1080 |
| TGGGATACAG | AAATATTTAT | GCTTCCGTTT | TTCATATATG | TGCATCCAAA | AGCGGCAAAG | 1140 |
| ACACTTTTGA | TGTACAGGTA | CAATATGCTG | GATGCAGCGA | GAAAAAATGC | GGCTTTAAAC | 1200 |
| GGGTATAAGG | GAGCACAATA | CCCTTGGGAA | TCTGCAGATA | CAGGAGAGGA | AGAGACACCT | 1260 |
| AAATGGGGAT | TTGATTACAT | GGGAAACCCT | GTAAGGATAT | GGACGGGTGA | TTTAGAGCAT | 1320 |
| CATATAACTG | CTGATATAGC | TTTTGCAGTG | TGGGAGTATT | TTAGAGCGAC | AGAGGATATT | 1380 |
| GAGTTTATGT | TGAATTACGG | TGCAGAAGTC | ATTTTTGAGA | CTGCAAGGTT | TTGGGTATCT | 1440 |
| AGATGTGAAT | ATGTAAAAGA | ATTAGACAGG | TATGAAATAA | ACAATGTCAT | AGGTCCTGAT | 1500 |
| GAATTTCATG | AGCATGTTGA | TAATAATGCT | TATACTGATT | ACCTTGCAAA | ATGGAATATT | 1560 |
| AAAAAGGGAC | TTGAACTAAT | CAATATGTTA | AAAGAAAAAT | ACCCTGAACA | TTATCATGCT | 1620 |
| ATATCAAACA | AGAAATGTTT | GACAAATGAG | GAAATGGAAA | AGTGGAAAGA | AGTTGAAGAA | 1680 |
| AAAATATATA | TACCTTATGA | CAAAGACAAA | AAGCTGATAG | AACAATTTGA | AGGCTATTTT | 1740 |
| GATAAAAAAG | ATTATGTTAT | TGATAAATTT | GATGAAAACA | ATATGCCTAT | ATGGCCTGAA | 1800 |
| GGTGTTGATA | TAACAAAATT | GGGTGATACC | CAGCTTATTA | AACAGGCTGA | TGTTGTTATG | 1860 |
| TTAATGCTTT | TGTTAGGTGA | GGAATTTGAC | GAAGAAACGA | AAAGAATCAA | TTACGAATAT | 1920 |
| TATGAAAAGC | GAACTATGCA | CAAATCTTCA | TTAGGTCCCA | GCATGTATGC | CATTATGGGG | 1980 |
| TTAAAAGTAG | GGGACCACAA | AAACGCATAT | CAGTCTTTCA | TGAGAAGTGC | CAACGTGGAC | 2040 |
| CTTGTGGACA | ATCAGGGGAA | CACTAAAGAA | GGTTTGCATG | CTGCATCTGC | TGGTGGTACA | 2100 |
| TGGCAAGTAG | TTGTTTTTGG | ATTTGGCGGA | ATGGAAATTG | ACAAGAAGG | GGCATTAAAT | 2160 |
| ATAAATTCGT | GGCTGCCAGA | AAAATGGGAT | AAACTTTCCT | ATAAAGTATT | TTGGAAAGGC | 2220 |
| AATTTAATAG | AGGTGATTGT | TACAAAACAG | GAAGTGACAG | TAAAAAAATT | AAAAGGAAAA | 2280 |

-continued

```
GGAAATATAA AAGTAAAGGT AAAAGGGAAA GAGCTGACAA TAGAA                    2325
```

(2) INFORMATION FOR SEQ ID NO:6:

(i) SEQUENCE CHARACTERISTICS:
        (A) LENGTH:10 amino acids
        (B) TYPE:amino acid
        (D) TOPOLOGY:linear (ii) MOLECULE TYPE:peptide (v) FRAGMENT TYPE:N-terminal fragment (xi) SEQUENCE DESCRIPTION:SEQ ID NO:6:

```
Met Val Lys His Met Phe Leu Glu Asp Val
1               5                   10
```

(2) INFORMATION FOR SEQ ID NO:7:

(i) SEQUENCE CHARACTERISTICS:
        (A) LENGTH:10 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:7:

```
Phe Asp Glu Asn Asn Met Pro Ile Trp Pro
1               5                   10
```

(2) INFORMATION FOR SEQ ID NO:8:

(i) SEQUENCE CHARACTERISTICS:
        (A) LENGTH:10 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:8:

```
Gly His Val Phe Trp Asp Thr Glu Ile Phe
1               5                   10
```

(2) INFORMATION FOR SEQ ID NO:9:

(i) SEQUENCE CHARACTERISTICS:
        (A) LENGTH:3956 base pairs
        (B) TYPE:nucleic acid
        (C) STRANDEDNESS:double
        (D) TOPOLOGY:linear (ii) MOLECULE TYPE:Genomic DNA (vi) ORIGINAL SOURCE:
        (A) ORGANISM:Thermoanaerobium brockii
        (F) STRAIN:ATCC 35047

(ix) FEATURE:
        (A1)NAME/KEY:1-100 5'-UTR
        (C1)IDENTIFICATION METHOD:E
        (A2)NAME/KEY:101-2425 mat peptide
        (C2)IDENTIFICATION METHOD:S
        (A3)NAME/KEY:2426-3956 3'-UTR
        (C3)IDENTIFICATION METHOD:E (xi) SEQUENCE DESCRIPTION:SEQ ID NO:9:

-continued

```
AGCTTGTAAT TAGAGATTCA GCTAGAAAGA TATAATTTTT TTTAAAAAGT ACCCAAAACG      60

TTTCGGATAA AATTTTTAGC AGGAATCAGG AGGTATATAA                           100

GTG GTA AAG CAC ATG TTT TTA GAG GAT GTA AAC AAT TTA ATA AGT GAT      148
Met Val Lys His Met Phe Leu Glu Asp Val Asn Asn Leu Ile Ser Asp
1               5                  10                  15

GAC AAA TGG CTT ATT TTC CAA AAT GAG TAT AAT ACA GAG GTA AAT CCT      196
Asp Lys Trp Leu Ile Phe Gln Asn Glu Tyr Asn Thr Glu Val Asn Pro
            20                  25                  30

CGA TAT GAG ACC CTT TTT ACA CTT ACA AAT GGT TAC ATG GGC GTA AGA      244
Arg Tyr Glu Thr Leu Phe Thr Leu Thr Asn Gly Tyr Met Gly Val Arg
        35                  40                  45

GGT ACT TTT GAG GAA GGA AGC GAG GGA GAA AGG TCG GGA AAT TTT ATT      292
Gly Thr Phe Glu Glu Gly Ser Glu Gly Glu Arg Ser Gly Asn Phe Ile
    50                  55                  60

GCA GGA ATT TTT GAC AAG TCA GAT GCG CAG GTT AGA GAA ATA GTA AAT      340
Ala Gly Ile Phe Asp Lys Ser Asp Ala Gln Val Arg Glu Ile Val Asn
65                  70                  75                  80

GCT CAA AAT TGG TTG AGA ATA AAG TTG TAT GTT GAA GGT GAA GAA TTA      388
Ala Gln Asn Trp Leu Arg Ile Lys Leu Tyr Val Glu Gly Glu Glu Leu
                85                  90                  95

AGT TTG GAT AAA TGC CAG TTG ATA GAA TTT AAA AGA ATT CTT GAT ATG      436
Ser Leu Asp Lys Cys Gln Leu Ile Glu Phe Lys Arg Ile Leu Asp Met
            100                 105                 110

AAA AAA GGT ATT CTA TTT AGG AGT ATG TTG ATA AAA GAC AGC AAA GAT      484
Lys Lys Gly Ile Leu Phe Arg Ser Met Leu Ile Lys Asp Ser Lys Asp
        115                 120                 125

AGA ATT ACT CGA ATT GAG GGA TAC AGG TTT ATA AGC CGT AGC GAC CTT      532
Arg Ile Thr Arg Ile Glu Gly Tyr Arg Phe Ile Ser Arg Ser Asp Leu
    130                 135                 140

CAT CGT TCT GCA ATT AAG CTA TTT GTA ACA CCT GTA AAT TAC AGT GGT      580
His Arg Ser Ala Ile Lys Leu Phe Val Thr Pro Val Asn Tyr Ser Gly
145                 150                 155                 160

GTT GTA GGT ATA GAG AGC ATT ATT GAT GGG ACT GTT TTA AAT TCA GCA      628
Val Val Gly Ile Glu Ser Ile Ile Asp Gly Thr Val Leu Asn Ser Ala
                165                 170                 175

GAT AGC CCA AAG CAT AGG GTA AAG CAT TTG AAA GTG GCT GAC AAT AGC      676
Asp Ser Pro Lys His Arg Val Lys His Leu Lys Val Ala Asp Asn Ser
            180                 185                 190

AGT TTA AAT AAA AGC GGA GTT TAT CTT GAA ACA GCA ACT ATT GAC GAT      724
Ser Leu Asn Lys Ser Gly Val Tyr Leu Glu Thr Ala Thr Ile Asp Asp
        195                 200                 205

GAT ATT CGC ATT GCA ACA GGT AGT GCA GTG AGG TTA TAT CAT TAT GAG      772
Asp Ile Arg Ile Ala Thr Gly Ser Ala Val Arg Leu Tyr His Tyr Glu
    210                 215                 220

GAT AAA GAG AAA AAT AAC ATA GCT AAA TTT AAG AGA TTT TTG CCT TTA      820
Asp Lys Glu Lys Asn Asn Ile Ala Lys Phe Lys Arg Phe Leu Pro Leu
225                 230                 235                 240

GGT GAA ATG AGT ATT GAA TAC TTT GAG TTT GAT GGC ACA GAG AAC AAA      868
Gly Glu Met Ser Ile Glu Tyr Phe Glu Phe Asp Gly Thr Glu Asn Lys
                245                 250                 255

ACA GTA GTA ATT GAC AAA TTT ATA ATA ACC TAT ACC TCA AGA GAC GTA      916
Thr Val Val Ile Asp Lys Phe Ile Ile Thr Tyr Thr Ser Arg Asp Val
            260                 265                 270

AAA AAA GGC CTA TTA AAG AGT ACG GTG GAA AAA GAA CTC TTT GCT TTT      964
Lys Lys Gly Leu Leu Lys Ser Thr Val Glu Lys Glu Leu Phe Ala Phe
        275                 280                 285

GCT GGA GAA GGT ATT GAC AAA GAG TTG CAG AGA CAT ATT GAG GTA TAT     1012
Ala Gly Glu Gly Ile Asp Lys Glu Leu Gln Arg His Ile Glu Val Tyr
    290                 295                 300
```

```
GAA GAA CTA TGG TCT GTT GCA GAT ATA AAT ATT GAA GGG GAT GAA GAA            1060
Glu Glu Leu Trp Ser Val Ala Asp Ile Asn Ile Glu Gly Asp Glu Glu
305                 310                 315                 320

GCA GAT AAA GCT TTG AGG TTT AAT ATT TTT CAT CTC ATG AGT TCT GTC            1108
Ala Asp Lys Ala Leu Arg Phe Asn Ile Phe His Leu Met Ser Ser Val
                325                 330                 335

AAT GAA AAT GAC CCC ATG GTA AGT ATC GCT GCA AAG GCC CTT CAT GGT            1156
Asn Glu Asn Asp Pro Met Val Ser Ile Ala Ala Lys Ala Leu His Gly
            340                 345                 350

GAG GGA TAC AAA GGC CAT GTC TTT TGG GAT ACA GAA ATA TTT ATG CTT            1204
Glu Gly Tyr Lys Gly His Val Phe Trp Asp Thr Glu Ile Phe Met Leu
        355                 360                 365

CCG TTT TTC ATA TAT GTG CAT CCA AAA GCG GCA AAG ACA CTT TTG ATG            1252
Pro Phe Phe Ile Tyr Val His Pro Lys Ala Ala Lys Thr Leu Leu Met
370                 375                 380

TAC AGG TAC AAT ATG CTG GAT GCA GCG AGA AAA AAT GCG GCT TTA AAC            1300
Tyr Arg Tyr Asn Met Leu Asp Ala Ala Arg Lys Asn Ala Ala Leu Asn
385                 390                 395                 400

GGG TAT AAG GGA GCA CAA TAC CCT TGG GAA TCT GCA GAT ACA GGA GAG            1348
Gly Tyr Lys Gly Ala Gln Tyr Pro Trp Glu Ser Ala Asp Thr Gly Glu
                405                 410                 415

GAA GAG ACA CCT AAA TGG GGA TTT GAT TAC ATG GGA AAC CCT GTA AGG            1396
Glu Glu Thr Pro Lys Trp Gly Phe Asp Tyr Met Gly Asn Pro Val Arg
            420                 425                 430

ATA TGG ACG GGT GAT TTA GAG CAT CAT ATA ACT GCT GAT ATA GCT TTT            1444
Ile Trp Thr Gly Asp Leu Glu His His Ile Thr Ala Asp Ile Ala Phe
        435                 440                 445

GCA GTG TGG GAG TAT TTT AGA GCG ACA GAG GAT ATT GAG TTT ATG TTG            1492
Ala Val Trp Glu Tyr Phe Arg Ala Thr Glu Asp Ile Glu Phe Met Leu
450                 455                 460

AAT TAC GGT GCA GAA GTC ATT TTT GAG ACT GCA AGG TTT TGG GTA TCT            1540
Asn Tyr Gly Ala Glu Val Ile Phe Glu Thr Ala Arg Phe Trp Val Ser
465                 470                 475                 480

AGA TGT GAA TAT GTA AAA GAA TTA GAC AGG TAT GAA ATA AAC AAT GTC            1588
Arg Cys Glu Tyr Val Lys Glu Leu Asp Arg Tyr Glu Ile Asn Asn Val
                485                 490                 495

ATA GGT CCT GAT GAA TTT CAT GAG CAT GTT GAT AAT AAT GCT TAT ACT            1636
Ile Gly Pro Asp Glu Phe His Glu His Val Asp Asn Asn Ala Tyr Thr
            500                 505                 510

GAT TAC CTT GCA AAA TGG AAT ATT AAA AAG GGA CTT GAA CTA ATC AAT            1684
Asp Tyr Leu Ala Lys Trp Asn Ile Lys Lys Gly Leu Glu Leu Ile Asn
        515                 520                 525

ATG TTA AAA GAA AAA TAC CCT GAA CAT TAT CAT GCT ATA TCA AAC AAG            1732
Met Leu Lys Glu Lys Tyr Pro Glu His Tyr His Ala Ile Ser Asn Lys
    530                 535                 540

AAA TGT TTG ACA AAT GAG GAA ATG GAA AAG TGG AAA GAA GTT GAA GAA            1780
Lys Cys Leu Thr Asn Glu Glu Met Glu Lys Trp Lys Glu Val Glu Glu
545                 550                 555                 560

AAA ATA TAT ATA CCT TAT GAC AAA GAC AAA AAG CTG ATA GAA CAA TTT            1828
Lys Ile Tyr Ile Pro Tyr Asp Lys Asp Lys Lys Leu Ile Glu Gln Phe
                565                 570                 575

GAA GGC TAT TTT GAT AAA AAA GAT TAT GTT ATT GAT AAA TTT GAT GAA            1876
Glu Gly Tyr Phe Asp Lys Lys Asp Tyr Val Ile Asp Lys Phe Asp Glu
            580                 585                 590

AAC AAT ATG CCT ATA TGG CCT GAA GGT GTT GAT ATA ACA AAA TTG GGT            1924
Asn Asn Met Pro Ile Trp Pro Glu Gly Val Asp Ile Thr Lys Leu Gly
        595                 600                 605

GAT ACC CAG CTT ATT AAA CAG GCT GAT GTT GTT ATG TTA ATG CTT TTG            1972
Asp Thr Gln Leu Ile Lys Gln Ala Asp Val Val Met Leu Met Leu Leu
```

-continued

```
       610                 615                 620
TTA GGT GAG GAA TTT GAC GAA GAA ACG AAA AGA ATC AAT TAC GAA TAT    2020
Leu Gly Glu Glu Phe Asp Glu Glu Thr Lys Arg Ile Asn Tyr Glu Tyr
625                 630                 635                 640

TAT GAA AAG CGA ACT ATG CAC AAA TCT TCA TTA GGT CCC AGC ATG TAT    2068
Tyr Glu Lys Arg Thr Met His Lys Ser Ser Leu Gly Pro Ser Met Tyr
                645                 650                 655

GCC ATT ATG GGG TTA AAA GTA GGG GAC CAC AAA AAC GCA TAT CAG TCT    2116
Ala Ile Met Gly Leu Lys Val Gly Asp His Lys Asn Ala Tyr Gln Ser
            660                 665                 670

TTC ATG AGA AGT GCC AAC GTG GAC CTT GTG GAC AAT CAG GGG AAC ACT    2164
Phe Met Arg Ser Ala Asn Val Asp Leu Val Asp Asn Gln Gly Asn Thr
        675                 680                 685

AAA GAA GGT TTG CAT GCT GCA TCT GCT GGT GGT ACA TGG CAA GTA GTT    2212
Lys Glu Gly Leu His Ala Ala Ser Ala Gly Gly Thr Trp Gln Val Val
    690                 695                 700

GTT TTT GGA TTT GGC GGA ATG GAA ATT GAC AAA GAA GGG GCA TTA AAT    2260
Val Phe Gly Phe Gly Gly Met Glu Ile Asp Lys Glu Gly Ala Leu Asn
705                 710                 715                 720

ATA AAT TCG TGG CTG CCA GAA AAA TGG GAT AAA CTT TCC TAT AAA GTA    2308
Ile Asn Ser Trp Leu Pro Glu Lys Trp Asp Lys Leu Ser Tyr Lys Val
                725                 730                 735

TTT TGG AAA GGC AAT TTA ATA GAG GTG ATT GTT ACA AAA CAG GAA GTG    2356
Phe Trp Lys Gly Asn Leu Ile Glu Val Ile Val Thr Lys Gln Glu Val
            740                 745                 750

ACA GTA AAA AAA TTA AAA GGA AAA GGA AAT ATA AAA GTA AAG GTA AAA    2404
Thr Val Lys Lys Leu Lys Gly Lys Gly Asn Ile Lys Val Lys Val Lys
        755                 760                 765

GGG AAA GAG CTG ACA ATA GAA                                        2425
Gly Lys Glu Leu Thr Ile Glu
    770                 775

TAGTCAAAAA GGTATAGGCA GGTGGATAAC CTGCTATACC TTAAAATAAA TTGATTATGT  2485

TTTAAGGGGG GATAAGTGGA GTTAGAGTAA AATTTTAAGT CCTCAATCAG ATATTTTACT  2545

ATAAAATTGT GAAAGGGGAA AGTGGTAATG AGTAAAAAAC TTTCAAGCAT CTTTGTATTG  2605

ACGATCTTTG TATTAGCTAC TGTTTTAGCT GGTTGTTCAT CCAGTAAAAA TAATACTTCC  2665

AGTGCCAATG AGACAAATAC ACAAAAACAA GAGACAGCAA AACCAGTTAC TATAAAATTA  2725

GGCATGTGGT CTTCATCTCC AGCAGAAAAG AAGATAGTGG ATGACCAAAT AGCTAAGTTT  2785

AAAGAAAAAT ATCCAAATAT AGATGTGCAA ATTGAGACAA TTGTGGGAGA TTACATGCAA  2845

AAATTACAAA CAGAACTGGC GTCAAATACA GCACCAGACA TATTCTATCT TGACAGAATG  2905

CCGGCACCAC AGCTTATGTC TTCAGGAGTT TTAGAGCCAT TAGATGATTA TATTAAGAAA  2965

TACAATGTGG ATGTAAATGA TTTCGAGCCA GCATTGCTTT CCGCTTTTCA GTGGGAGGGA  3025

AAAACTTATG GTTACCAAA GGATTTCAAT ACTCTAGCTT TGTTTTACAA CAAAGACATG  3085

TTTAAAGCGG CTGGAATAAA TGAGCCTCCA AAAACATGGG AGGAATTAAG AGATGTAGCT  3145

AAAAAGTTGA CAAAGACGG TGTCAAAGGT TTGGTTTTAT CAGCGAGACCT TGCAAGATTT  3205

GATGCTTTTA TAAATCAAAA TGGCGGTTCA GTATATCAAG GATGGAAAAG TTACTTTAAA  3265

TCTGCCAGAG AATGCACAAG CTCTTGATTT TTATGTAGGC CTCATTACAA AAGACAAAGT  3325

TACTGACACA CCACAAAACA TGGGAGAAGG CTGGAATGGA GATGCTTTTG CTGCTAAAAA  3385

AGCTGCAATG GCAATAGAAG GTGGCTGGAT GATACCATTC CTCAAAGAAA AAGCTCCTGA  3445

TTTAAACTAT GGTATAGCAG AGCTTCCAGC AGGAAAGCAA AAATCTACAA TGGCTTTCAC  3505

TGTTGCATAT GTGATGAATA AAAACAGCAA ACATAAAGAT GAAGCCTTTA AACTTATTGA  3565
```

```
ATTTTTAACC GGTAAAGAAG GACAGCAATT TGTAGTAGAT TCAGGCCTTG CACTTCCATC       3625

GAGAAAGTCT ATGCAAGAAG GATTTAAGGA GAAATATCCT GAAAGAGCTG CCTTTGTAGA       3685

TGGTGCTTCT TATGCGGTAC CATGGCAATT CGGTTTGTAT GGCACAAAGG TAGTAGATGC       3745

GGCTAATAAA GCCTGTGAAG CATTAATAAT GAAGCAAATA AGTAGTGCTC AGCAAGCTCT       3805

TGACAACGCA CAAAGGAAG TTGGACAATA ATTTAAGTAA GCAGCACCTT ACTAAAATAA        3865

GGTGCTGCAA TTATGATTTT TTAAGGTTGA AGGGAAGGAT GTATTTATGG AAGCTAAAAT       3925

GACTATGAAA AAGAGGTATT TATACGAAGC T                                      3956

(2) INFORMATION FOR SEQ ID NO:10:

(i) SEQUENCE CHARACTERISTICS:
        (A) LENGTH:20 base pairs
        (B) TYPE:nucleic acid
        (C) STRANDEDNESS:double
        (D) TOPOLOGY:linear (xi) SEQUENCE DESCRIPTION:SEQ ID NO:10:

TTYGAYGARA AYAAYATGCC                                                     20
```